(12) United States Patent
Ranieri et al.

(10) Patent No.: US 10,809,270 B2
(45) Date of Patent: Oct. 20, 2020

(54) METHODS FOR SCREENING FOR FETAL TRISOMIES

(71) Applicant: MEDVET SCIENCE PTY LTD, Underdale, South Australia (AU)

(72) Inventors: Enzo Ranieri, Woodville (AU); Steven Ramsay, Viewbank (AU); Peter Charles Kinmont Sharp, Myrtle Bank (AU); Janice Fletcher, Medindie (AU)

(73) Assignee: AUSHEALTH CORPORATE PTY LTD, Underdale, South Australia (AU)

( * ) Notice: Subject to any disclaimer, the term of this patent is extended or adjusted under 35 U.S.C. 154(b) by 238 days.

(21) Appl. No.: 15/578,596

(22) PCT Filed: Jun. 2, 2016

(86) PCT No.: PCT/AU2016/050443
§ 371 (c)(1),
(2) Date: Nov. 30, 2017

(87) PCT Pub. No.: WO2016/191818
PCT Pub. Date: Dec. 8, 2016

(65) Prior Publication Data
US 2018/0156812 A1  Jun. 7, 2018

(30) Foreign Application Priority Data

Jun. 2, 2015  (AU) .............................. 2015902036
Dec. 21, 2015  (WO) ................ PCT/AU2015/050823

(51) Int. Cl.
*G01N 33/68* (2006.01)
*G01N 33/92* (2006.01)
*G01N 33/483* (2006.01)
*G16H 10/40* (2018.01)

(52) U.S. Cl.
CPC ......... *G01N 33/689* (2013.01); *G01N 33/483* (2013.01); *G01N 33/6848* (2013.01); *G01N 33/92* (2013.01); *G16H 10/40* (2018.01); *G01N 2800/387* (2013.01)

(58) Field of Classification Search
CPC . G01N 33/689; G01N 2800/387; G16H 10/40
See application file for complete search history.

(56) References Cited

U.S. PATENT DOCUMENTS

2013/0344503 A1   12/2013   Cuckle et al.

FOREIGN PATENT DOCUMENTS

| CA | 2739315 A1 | 11/2012 |
| WO | WO-2012/101268 A1 | 8/2012 |
| WO | WO 2016/191793 | 12/2016 |

OTHER PUBLICATIONS

Borell, Antoni et al. "First-trimester screening for trisomy 21 combining biochemistry and ultrasound at individually optimal gestational ages. An interventional study." Prenatal Diagnosis (2004) 24 541-545. (Year: 2004).*
Adelekan et al., Lipid profiles of children with Down syndrome compared with their siblings, Pediatrics, 129(6):e1382-7 (2012).
Bocconi et al., Trisomy 21 is associated with hypercholesterolemia during intrauterine life, Am. J. Obstet. Gynecol., 176(3):540-3 (1997).
Charkiewicz et al., Maternal plasma and amniotic fluid sphingolipids profiling in fetal Down syndrome, PLoS One, 10(5):e0127732 (2015).
International Application No. PCT/AU2016/050443, International Search Report and Written Opinion, dated Aug. 2, 2016.
Lam et al., Decreased cholesterol synthesis as a possible aetiological factor in malformations of trisomy 18, Eur. J. Med. Genet., 49(2):195-9 (2006).
Pinto et al., Impact of fetal chromosomal disorders on maternal blood metabolome: toward new biomarkers?, Am. J. Obstet. Gynecol., 213(6):841.e1-841.e15 (2015).
Pinto et al., Maternal plasma phospholipids are altered in trisomy 21 cases and prior to preeclampsia and preterm outcomes, Rapid Commun. Mass Spectrom., 28(14):1635-8 (2014).
Bligh et al., A rapid method of total lipid extraction and purification, Canadian J. Biochem. Physiol., 37(8):911-7 (1959).
Dennis et al., A mouse macrophage lipidome, J. Biol. chem., 285(51):39976-85 (Dec. 2010).
European Application No. 16802248.1, Communication Pursuant to Article 9493) EPC, dated Oct. 9, 2019.
Folch et al., A simple method for the isolation and purification of total lipides from animal tissues, J. Biol. Chem., 226: 497-509 (1957).
Meikle et al., Plasma lipidomic analysis of stable and unstable coronary artery disease, Arterioscler. Thromb. Vasc. Biol., 31(11):2723-32 (Nov. 2011).
Muniandy et al., A semi-automated lipid extraction protocol using the Agilent bravo automated liquid handling platform, Agilent Technologies, Inc., Application Note (5991-5724EN) (2015).
Quehenberger et al., Lipidomics reveals a remarkable diversity of lipids in human plasma, J. Lipid Res., 51(11):3299-305 (Nov. 2010).
Sanchez-Ribas et al., Differential metabolic profiling of non-pure trisomy 21 human preimplantation embryos, Fertil. Steril., 98(5):1157-64.e1-2 (Nov. 2012).
Sandra et al., Comprehensive blood plasma lipidomics by liquid chromatography/quadrupole time-of-flight mass spectrometry, J. Chromatogr. A, 1217(25):4087-99 (Jun. 2010).

(Continued)

*Primary Examiner* — Christopher Adam Hixson
(74) *Attorney, Agent, or Firm* — Marshall, Gerstein & Borun LLP

(57) ABSTRACT

The present disclosure relates to methods for screening and identifying a fetal trisomy. Certain embodiments of the present disclosure provide a method of screening for a fetal trisomy in a pregnant female subject. The method comprises detecting one or more lipid markers from the subject, wherein the one or more markers is indicative of the risk of a fetal trisomy in the subject, and determining the risk of a fetal trisomy in the pregnant female subject on the basis of the one or more lipid markers detected.

10 Claims, 7 Drawing Sheets

(56) References Cited

OTHER PUBLICATIONS

Bahado-Singh et al., Metabolomic analysis for first-trimester Down syndrome prediction, Am. J. Obstet. Gynecol., 208(5):371.e1-8 (May 2013).
European Patent Application No. 16802248, Supplementary European Search Report dated Nov. 9, 2018.
Kolialexi et al., Proteomics in prenatal diagnosis, Expert Rev. Proteomics, 6(2):111-3 (Apr. 2006).
Singapore Patent Application No. 11201709958X, Written Opinion, dated Dec. 13, 2018.
Tansley et al., Sterol lipid metabolism in down syndrome revisited: down syndrome is associated with a selective reduction in serum brassicasterol levels, Curr. Gerontol. Geriatr. Res., 2012:179318 (2012).

* cited by examiner

Fig. 1

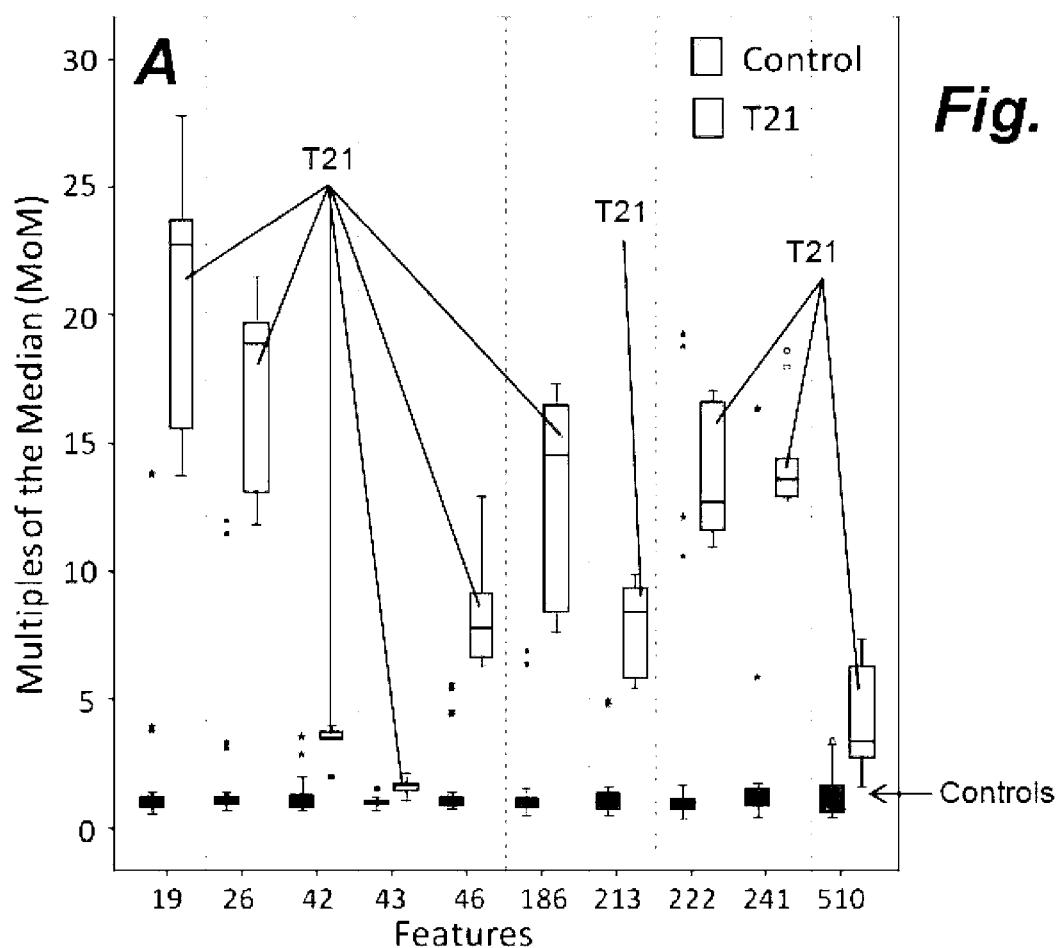
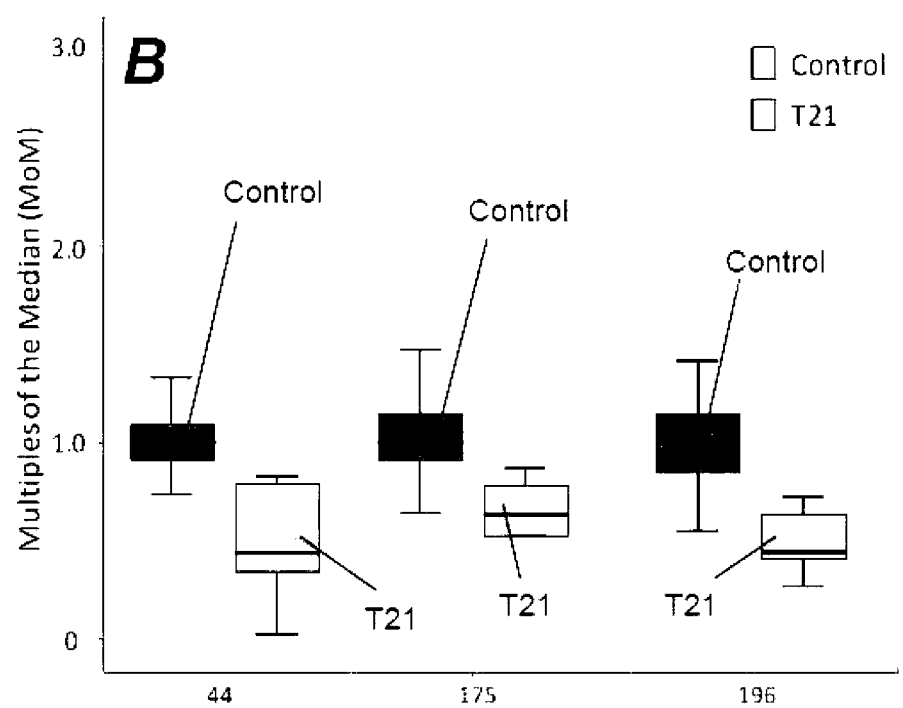
Fig. 3

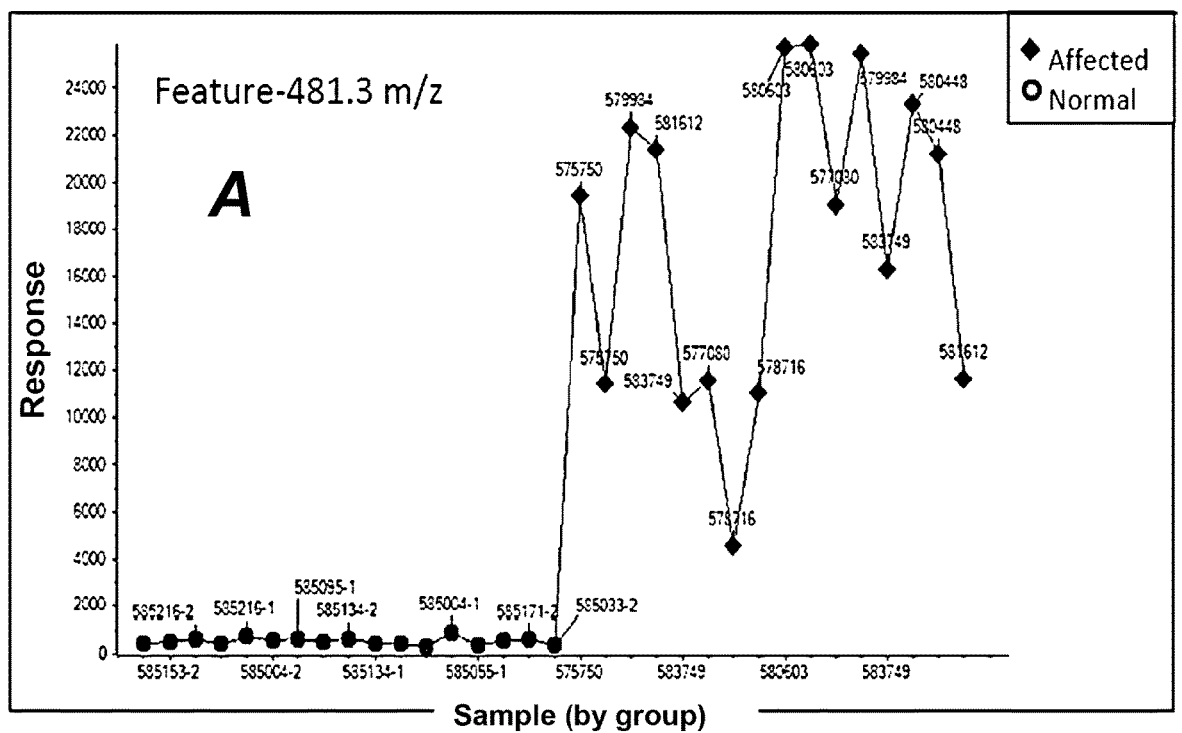
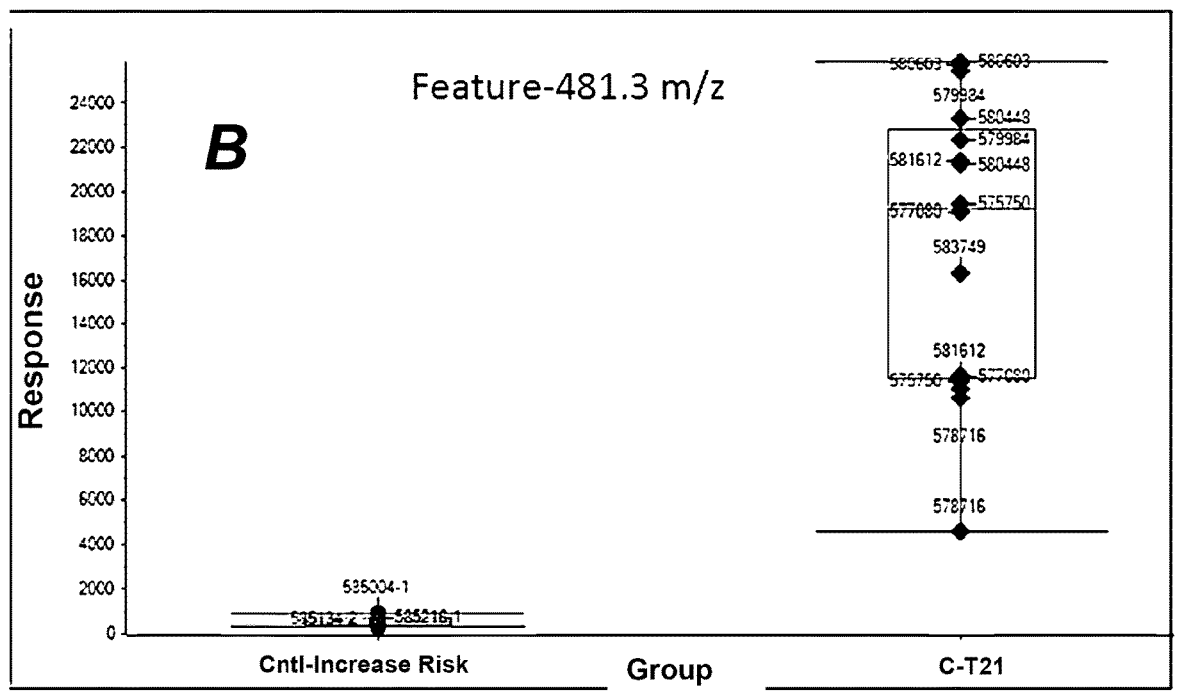
Fig. 5

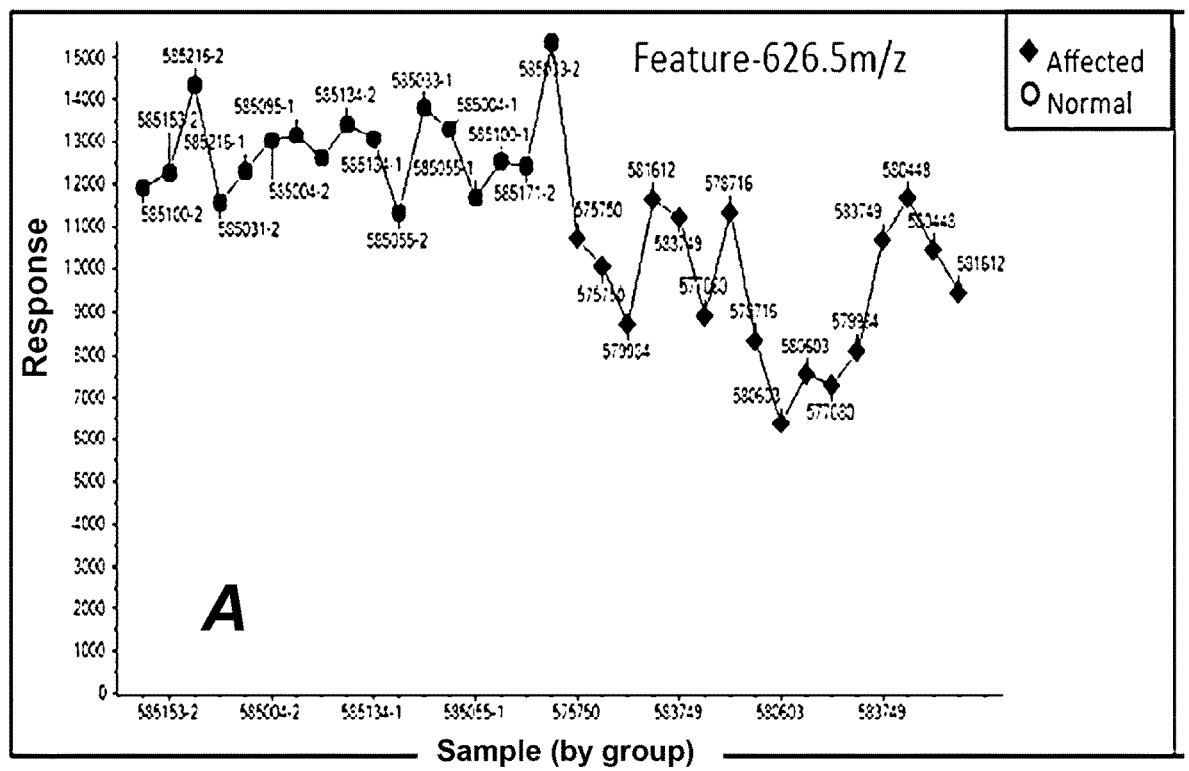
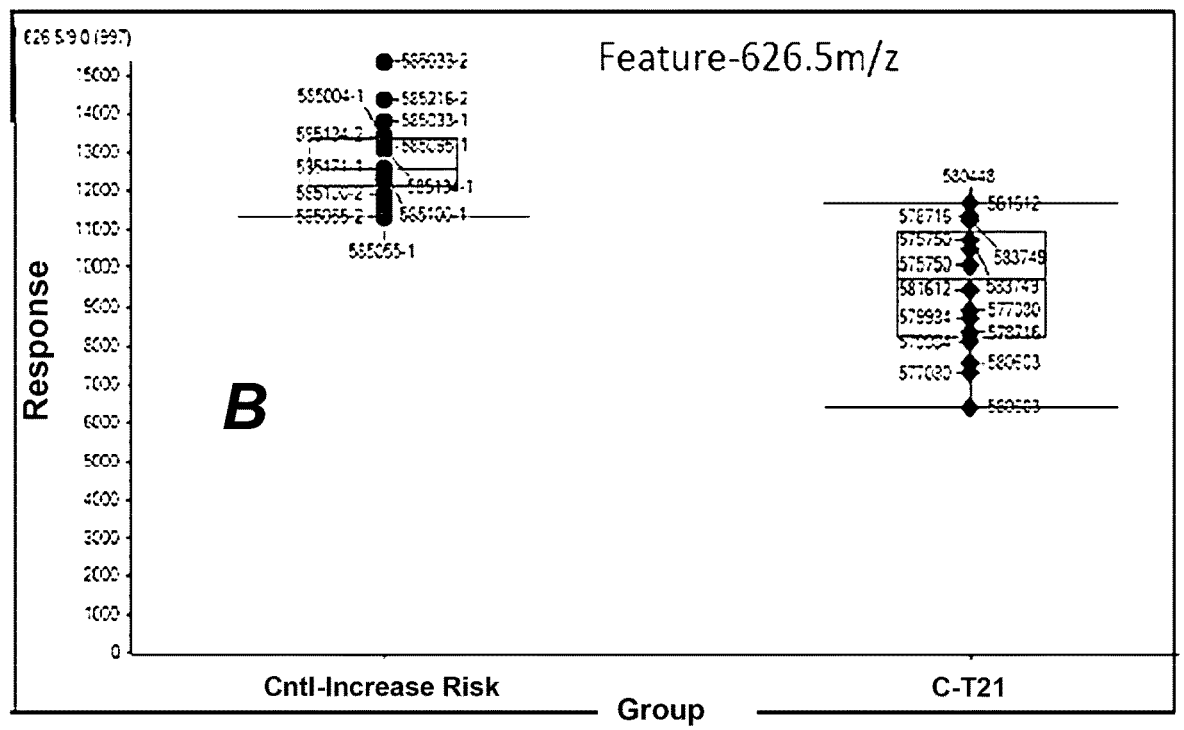
Fig. 6

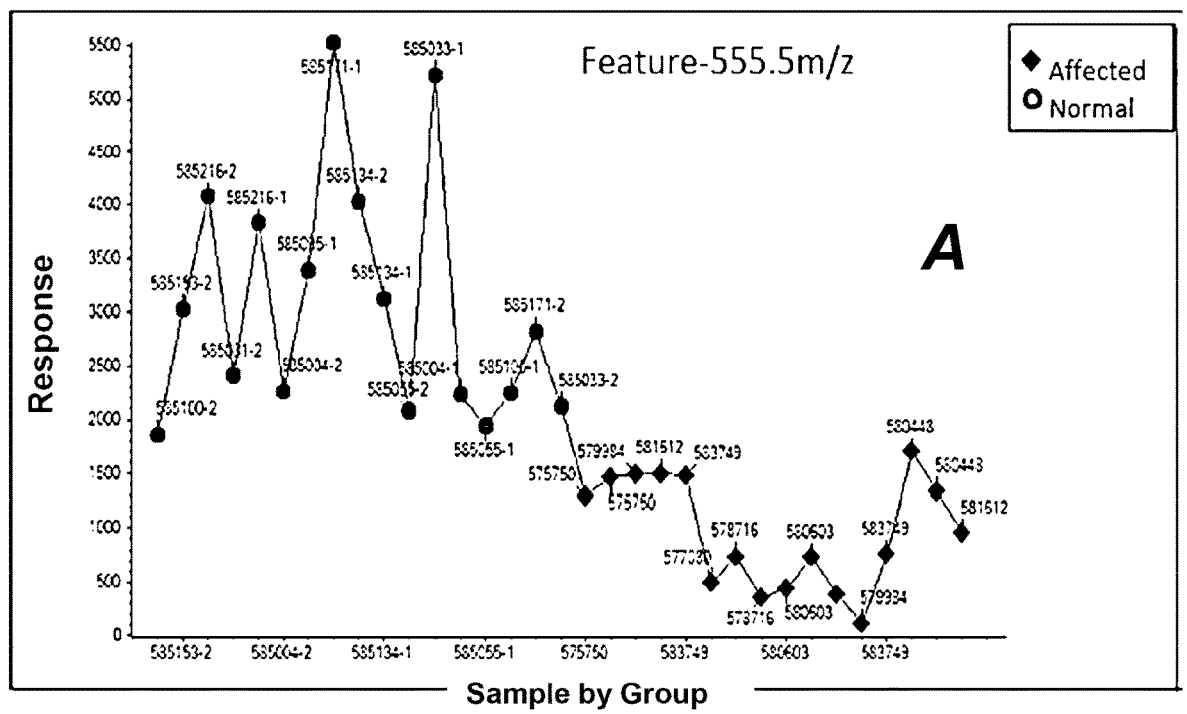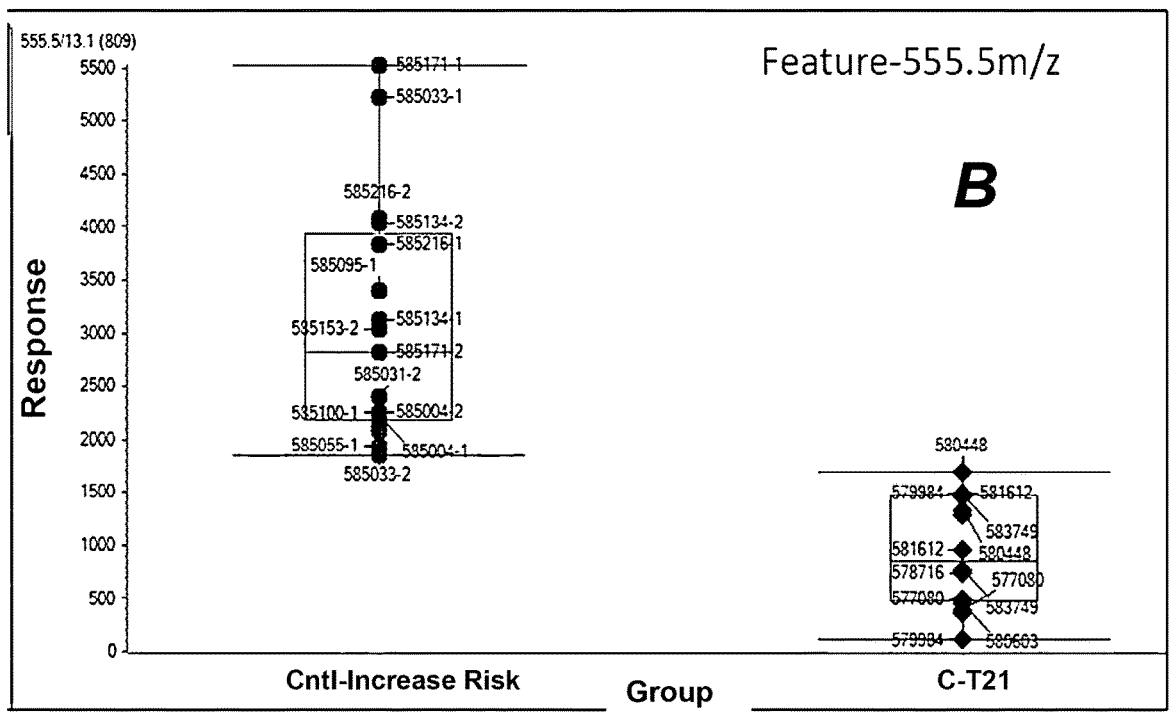
Fig. 7

METHODS FOR SCREENING FOR FETAL TRISOMIES

PRIORITY CLAIM

This application claims priority to Australian provisional patent application number 2015902036 filed on 2 Jun. 2015 and international patent application PCT/AU2015/050823 filed on 21 Dec. 2015, the contents of which are both hereby incorporated by reference.

FIELD

The present disclosure relates to methods for screening and identifying a fetal trisomy.

BACKGROUND

Pre-natal screening is routinely undertaken in most developed countries. Pre-natal screening often includes nuchal translucency testing by ultrasound, testing of maternal blood for chromosomal abnormalities and/or other abnormalities, chorionic villus sampling (CVS) to test for a number of physical and intellectual conditions that may affect the fetus, amniocentesis and cordocentesis. In some cases where pre-natal screening indicates an increased risk of a fetus having an abnormality, pre-natal diagnostic tests can also be employed to better determine whether the fetus is likely to be affected.

Some pre-natal screening carries an increased risk of adverse outcomes for the fetus and/or the mother. For example, amniocentesis and chorionic villus sampling both carry an increased risk of a miscarriage occurring due to the test being invasive. As such, there are significant benefits to pre-natal screening that does not carry such risks, such as pre-natal screening that involves testing of maternal blood.

A large proportion of the pre-natal screening undertaken currently involves pre-natal screening for chromosomal abnormalities in the fetus, as the frequency for such abnormalities is significant. For example, in the United States the frequency of chromosomal abnormalities is in the order of 1 in 150 pregnancies.

A common form of chromosomal abnormality is a trisomy. This type of chromosomal abnormality involves one or more additional copies of a chromosome (or a part of a chromosome) and includes trisomies of chromosomes 21, 18, 13, 9, 8 and 22. For example, Down syndrome is caused by having an extra copy of chromosome 21.

Down syndrome is the most common form of chromosome abnormality detected in prenatal diagnosis. Its prevalence is strongly associated with maternal age and definitive prenatal diagnosis is accomplished by assessment of the fetal karyotype using a sample of fetal cells obtained by amniocentesis or CVS. However, the current invasive prenatal diagnosis is associated with a high risk (~1%) of miscarriage. Similarly, trisomy of chromosome 18 (Edwards syndrome) is diagnosed by assessment of fetal karyotype.

The current tests for prenatal screening and prenatal diagnosis of fetal aneuploidies suffer from one or more disadvantages. For example, many of the current tests are either invasive, time consuming, require a high degree of technical skill to perform, lack sufficient specificity and/or sensitivity, have a high false negative rate, require separation of maternal and fetal DNAs or RNAs, or require retrieval of cells of fetal origin.

Accordingly, there is a need for new methods of prenatal screening and/or prenatal diagnosis for fetal trisomies, and in particular new methods for prenatal screening and/or prenatal diagnosis that address one or more problems and/or to provide one or more advantages.

SUMMARY

The present disclosure relates to methods, products and kits for screening, identifying or assessing the risk of a fetal trisomy, and to methods for identifying markers indicative of the risk of a fetal trisomy.

Certain embodiments of the present disclosure provide a method of screening for a fetal trisomy in a pregnant female subject, the method comprising:
  detecting one or more lipid markers from the subject, wherein the one or more markers is indicative of the risk of a fetal trisomy in the subject; and
  determining the risk of a fetal trisomy in the pregnant female subject on the basis of the one or more lipid markers detected.

Certain embodiments of the present disclosure provide a method of screening for a fetal trisomy in a pregnant female subject, the method comprising:
  detecting one or more lipid markers from the subject, wherein the one or more lipid markers is indicative of the risk of a fetal trisomy in the subject; and
  determining the presence or absence of a fetal trisomy in the pregnant female subject on the basis of the one or more lipid markers detected.

Certain embodiments of the present disclosure provide a method of screening for a fetal trisomy in a pregnant female subject, the method comprising:
  processing a biological sample from the subject to allow detection of lipid markers;
  detecting one or more lipid markers in the processed sample indicative of the risk of a fetal trisomy in the subject; and
  determining the risk of a fetal trisomy in the pregnant female subject on the basis of the one or more lipid markers detected.

Certain embodiments of the present disclosure provide a method of screening for a fetal trisomy in a pregnant female subject, the method comprising:
  processing a biological sample from the subject to allow detection of lipid markers by mass spectrometry;
  detecting by mass spectrometry one or more lipid markers in the processed sample indicative of the risk of a fetal trisomy in the subject; and
  determining the risk of a fetal trisomy in the pregnant female subject on the basis of the one or more lipid markers detected.

Certain embodiments of the present disclosure provide a mass spectrographic method of screening for a fetal trisomy in a pregnant female subject, the method comprising:
  processing a biological sample from the subject to allow detection of lipid markers;
  detecting one or more lipid markers in the processed sample indicative of the risk of a fetal trisomy in the subject; and
  determining the risk of a fetal trisomy in the pregnant female subject on the basis of the one or more lipid markers detected.

Certain embodiments of the present disclosure provide a method of screening for a fetal trisomy in a pregnant female subject, the method comprising:
  detecting one or more lipid markers from the subject, wherein the one or more lipid markers is indicative of the risk of a fetal trisomy in the subject;

using a computer processor means to process data associated with the presence and/or level of the one or more lipid markers detected to generate a likelihood and/or risk of the presence or absence of a fetal trisomy; and determining the risk of the presence or absence of a fetal trisomy in the pregnant female subject on the basis of the likelihood and/or risk generated.

Certain embodiments of the present disclosure provide a computer-readable medium encoded with programming instructions executable by a computer processor means to allow the computer processor means to receive data associated with the presence and/or level of one or more lipid markers indicative of the risk of a fetal trisomy in a subject and process the data to generate a likelihood and/or risk of the presence or absence of a fetal trisomy in the subject.

Certain embodiments of the present disclosure provide use of a mass spectrometer to detect one or more lipid markers from a biological sample of a pregnant female subject, wherein the one or more lipid markers are indicative of the risk of a fetal trisomy in the pregnant female.

Certain embodiments of the present disclosure provide a method of identifying the presence or absence of a fetal trisomy in a pregnant female subject, the method comprising:
    detecting one or more lipid markers from the subject, wherein the one or more lipid markers is indicative of risk of a fetal trisomy in the subject; and
    identifying the presence or absence of a fetal trisomy in the pregnant female subject on the basis of the one or more lipid markers detected.

Certain embodiments of the present disclosure provide a method of identifying the presence or absence of a fetal trisomy in a pregnant female subject, the method comprising:
    processing a biological sample from the subject to allow detection of lipid markers;
    detecting one or more lipid markers in the processed sample indicative of the risk of a fetal trisomy in the subject; and
    identifying the presence or absence of a fetal trisomy in the pregnant female subject on the basis of the one or more lipid markers detected.

Certain embodiments of the present disclosure provide a method of identifying the presence or absence of a fetal trisomy in a pregnant female subject, the method comprising:
    processing a biological sample from the subject to allow detection of lipid markers by mass spectrometry;
    detecting by mass spectrometry one or more lipid markers in the processed sample indicative of the risk of a fetal trisomy in the subject; and
    identifying the presence or absence of a fetal trisomy in the pregnant female subject on the basis of the one or more lipid markers detected.

Certain embodiments of the present disclosure provide a mass spectrographic method of identifying the presence or absence of a fetal trisomy in a pregnant female subject, the method comprising:
    processing a biological sample from the subject to allow detection of lipid markers;
    detecting by mass spectrometry one or more lipid markers in the processed sample indicative of the risk of a fetal trisomy in the subject; and
    identifying the presence or absence of a fetal trisomy in the pregnant female subject on the basis of the one or more lipid markers detected.

Certain embodiments of the present disclosure provide a method of identifying the presence or absence of a fetal trisomy in a pregnant female subject, the method comprising:
    detecting one or more lipid markers from the subject, wherein the one or more lipid markers is indicative of the risk of a fetal trisomy in the subject; and
    using a computer processor means to process data associated with the presence and/or level of the one or more lipid markers to generate a likelihood and/or risk of the presence or absence of a fetal trisomy; and
    identifying the presence or absence of a fetal trisomy in the pregnant female subject on the basis of the likelihood and/or risk generated.

Certain embodiments of the present disclosure provide a method of determining the risk of a pregnant female subject carrying a fetus with a trisomy, the method comprising:
    detecting one or more lipid markers from the subject, wherein the one or more markers is indicative of the risk of a fetal trisomy in the subject; and
    determining the risk of the subject carrying a fetus with a trisomy on the basis of the one or more lipid markers detected.

Certain embodiments of the present disclosure provide a method of identifying one or more lipid markers indicative of the risk of a fetal trisomy, the method comprising:
    identifying one or more lipid markers which are differentially present between a pregnant female subject having a fetal trisomy and a pregnant female subject without a fetal trisomy; and
    identifying the one or more lipid markers as one or more lipid markers indicative of the risk of a fetal trisomy.

Certain embodiments of the present disclosure provide a method of identifying one or more lipid markers indicative of the presence or absence a fetal trisomy, the method comprising:
    identifying one or more lipid markers which are differentially present between a pregnant female subject having a fetal trisomy and a pregnant female subject without a fetal trisomy; and
    identifying the one or more lipid markers as one or more lipid markers indicative of the presence or absence of a fetal trisomy.

Certain embodiments of the present disclosure provide a method of identifying one or more lipid markers indicative of the risk of a fetal trisomy, the method comprising identifying a plurality of lipid markers which in combination are indicative of the risk of a fetal trisomy.

Certain embodiments of the present disclosure provide a kit for performing a method as described herein.

Other embodiments are disclosed herein.

BRIEF DESCRIPTION OF THE FIGURES

Certain embodiments are illustrated by the following figures. It is to be understood that the following description is for the purpose of describing particular embodiments only and is not intended to be limiting with respect to the description.

FIG. 1 shows results from t-test of trisomy 21 and unaffected controls. 1 denotes unaffected controls, 2 denotes trisomy 21. Ordered using p-value (not all shown). These features differentiate trisomy 21 from normal unaffected pregnancy.

FIG. 3 represents the MoM plot for each feature showing either an upregulated (3A) or down-regulated response (3B). The calculation of MoM performed by dividing each response of the feature by the median response for the unaffected population. Features for 3A, index #19, m/z 367.3, index #26, m/z 369.3, index #42, m/z 429.4, index #43, m/z 429.4, index #46, m/z 445.4, index #186, m/z 680.6, index #213, m/z 703.6, index #222, m/z 711.6, index #241, m/z 727.6, & 510, m/z 890.8. For 3B index #44, m/z 431.4, index #175, m/z 670.6 & index #196, m/z 688.6.

FIG. 5 shows the data for feature mass 481.3239 between T21 and controls.

FIG. 6 shows the data for feature mass 626.4979 between T21 and controls.

FIG. 7 shows the data for feature mass 555.5448 between T21 and controls.

DETAILED DESCRIPTION

Figure 2:
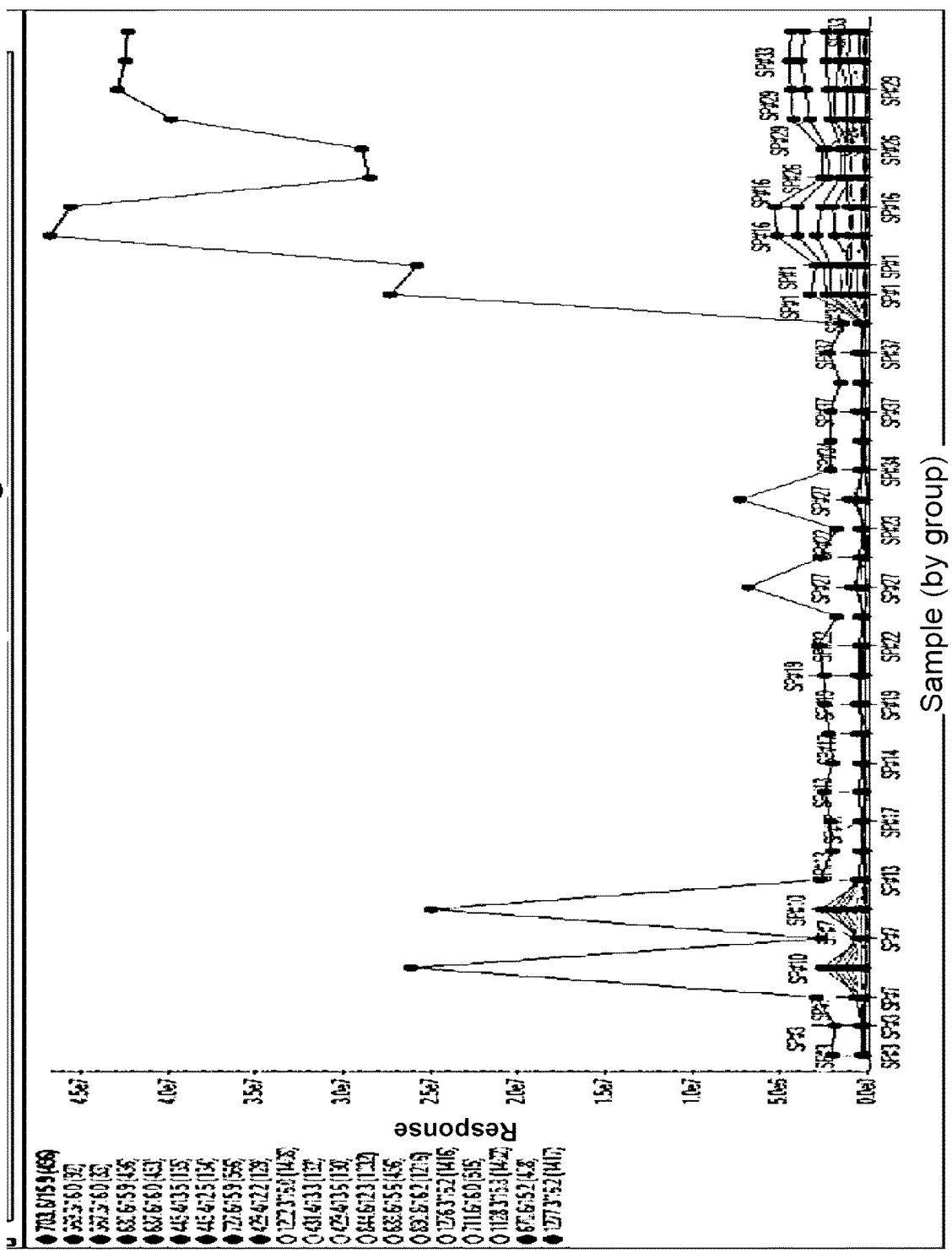
FIG. 2 shows a selection of profile plots of individual ions of the top 20 most significant individual m/z ions showing relative differences.

The present disclosure relates to methods, products and kits for screening or identifying a fetal trisomy and to methods for identifying markers indicative of the risk of a fetal trisomy.

The present disclosure arises from the recognition that a non-targeted global metabolite profiling approach may be used to identify potential markers associated with fetal abnormalities. Using this approach, specific classes of lipid markers have been identified that are indicative of the presence or absence of fetal trisomies.

Certain disclosed embodiments have one or more combinations of advantages. For example, some of the advantages of the embodiments disclosed herein include one or more of the following: an improved method for screening and/or identifying fetal trisomies; methods for assessing the likelihood or risk of a fetal trisomy; the use of new markers for screening and/or identifying fetal trisomies, or for assessing the likelihood or risk of a fetal trisomy; methods for screening and/or identifying fetal trisomies that can be performed if desired using mass/charge (m/z) analysis; methods for screening and/or identifying fetal trisomies that do not carry a substantially increased adverse risk to the mother and/or fetus; the use of one or more non-nucleic acid markers for screening and/or identifying fetal trisomies; the use of one or more non-protein/non-polypeptide markers for screening and/or identifying fetal trisomies; methods for identifying new markers for screening for the presence and/or absence of fetal trisomies; methods for screening and/or identifying fetal trisomies that can utilize mass spectrometric analysis; to identify specific lipids of class and/or mass which alone, or in combination, are predictive of the risk of a fetal trisomy; to address one or more problems in the art; to provide one or more advantages in the art; or to provide a useful commercial choice. Other advantages of certain embodiments are disclosed herein.

Certain embodiments of the present disclosure provide a method of screening for a fetal trisomy in a pregnant female subject.

Certain embodiments of the present disclosure provide a method of screening for a fetal trisomy in a pregnant female subject, the method comprising:

detecting one or more lipid markers from the subject, wherein the one or more markers is indicative of the risk of a fetal trisomy in the subject; and determining the risk of a fetal trisomy in the pregnant female subject on the basis of the one or more lipid markers detected.

In certain embodiments, the method is used for prenatal screening. In certain embodiments, the method is used for prenatal diagnosis.

In certain embodiments, the one or more lipid markers are indicative of the presence or absence of a fetal trisomy. In certain embodiments, the one or more lipid markers are indicative of the presence of a fetal trisomy. In certain embodiments, the one or more lipid markers are indicative of the absence of a fetal trisomy. In certain embodiments, the one or more lipid markers are indicative of the likelihood or risk of a fetal trisomy.

In certain embodiments, the one or more markers is indicative of an increased risk of a fetal trisomy, a low or normal risk of a fetal trisomy, and/or the presence or absence of a fetal trisomy.

Certain embodiments of the present disclosure provide a method of screening for a fetal trisomy in a pregnant female subject, the method comprising:

detecting one or more lipid markers from the subject, wherein the one or more markers is indicative of the presence or absence of a fetal trisomy in the subject; and determining the presence or absence of a fetal trisomy in the pregnant female subject on the basis of the one or more lipid markers detected.

In certain embodiments, the method of screening is used to screen for the presence or absence of a fetal trisomy, to identify a fetal trisomy in a pregnant female subject, to identify the absence of a fetal trisomy in a pregnant female subject, to exclude an abnormal pregnancy in a pregnant female subject, to identify the likelihood and/or risk of a fetal trisomy, to assess the likelihood or risk of a trisomy, for prenatal screening, for prenatal testing and for prenatal diagnosis.

Certain embodiments of the present disclosure provide a method of identifying the presence of a fetal trisomy in a subject.

Certain embodiments of the present disclosure provide a method of excluding the presence of a fetal trisomy in a subject.

Certain embodiments of the present disclosure provide a method of determining the risk of a pregnant female subject carrying a fetus with a trisomy.

The term "lipid" refers to a hydrophobic or amphipathic molecule. Examples of biological lipids comprise fatty acids, glycerolipids, glycerophospholipids, sphingolipids, sterol lipids, prenol lipids, saccharolipids, polyketides, waxes, eicosanoids, monoglycerides, diglycerides, triglycerides, phospholipids, sphingolipids, terpenes and fat-soluble vitamins. The main classes and sub-classes of lipids are as described in the Lipid Maps Consortium resource, found at http.//www.lipidmaps.org/ and described in Fahy E. et al (2009) *Journal of Lipid Research* April; 50 Suppl:S9-14.

The term "lipid" also includes fragments of lipids and/or ions (positive and/or negative) of lipids, for example as produced and/or detected by mass spectrometric methods (typically with a mass tolerance of +/−20 ppm) and also to any adducts of a lipid which are formed and subsequently measured or detected. For example, a sample may be treated to form adducts to the lipids and the lipid adduct is then subsequently detected. In this regard, any molecular weights or m/z value referred to herein refer to a lipid without an adduct, and it will be appreciated that if a lipid is being measured or detected as an adduct, then molecular weight of the adduct will be taken into account.

A trisomy is typically a form of polysomy in which there are three instances of a particular chromosome (or a part of chromosome) instead of the normal two. However it should be understood that the term also refers to a trisomy that is a translocation trisomy and/or a mosaic trisomy. Examples of trisomies include a trisomy of chromosome 21 (Down syndrome), chromosome 18 (Edwards syndrome), chromosome 13 (Patau syndrome), chromosome 9, chromosome 8 (Warkany syndrome 2) and chromosome 22.

In certain embodiments, the fetal trisomy comprises trisomy 21. In certain embodiments, the fetal trisomy comprises trisomy 18.

In certain embodiments, the trisomy is a trisomy involving an extra chromosome. In certain embodiments, the trisomy is a mosaic trisomy. In certain embodiments, the trisomy is a translocation trisomy. In certain embodiments, the trisomy is a trisomy 21 involving an extra chromosome. In certain embodiments, the trisomy is a mosaic trisomy 21. In certain embodiments, the trisomy is a translocation trisomy 21 (for example onto the 13th, 14th or 15th chromosome).

In certain embodiments, the subject is a human subject.

In certain embodiments, the subject is a mammalian subject. In certain embodiments, the subject is an animal. In certain embodiments, the subject is a livestock animal (such as a horse, a cow, a sheep, a goat, a pig), a domestic animal (such as a dog or a cat) or other type of animal such as a primate, a rabbit, a rat, a mouse, a bird and a laboratory animal. Applications to screening for fetal trisomies in animals are contemplated. Animal models for identifying markers are contemplated.

In certain embodiments, the subject is a pregnant female subject or a subject suspected of being pregnant.

In certain embodiments, the pregnant human female subject is a subject in the first trimester of pregnancy. In certain embodiments, the method comprises detecting the one or more lipid markers in the first trimester of pregnancy.

In certain embodiments, the pregnant female subject is a subject in the second trimester of pregnancy. In certain embodiments, the method comprises detecting the one or more lipid markers in the second trimester of pregnancy.

In certain embodiments, the subject has an increased risk or likelihood of suffering from, or being susceptible to, a fetal trisomy. In certain embodiments, the subject has an age of 30 years or over, 35 years or over, or 40 years or over.

In certain embodiments, the method comprises detecting a single marker. In certain embodiments, the method comprises detecting a plurality of markers. In certain embodiments, the method comprises detecting 2 or more markers, 3 or more markers, 4 or more markers, or 5 or more markers. In certain embodiments, the method comprises detecting at least 2 markers, at least 3 markers, at least 4 markers, or at least 5 markers. In certain embodiments, the method comprises detecting a plurality of markers. In certain embodiments, the method comprises detecting a combination of markers.

In certain embodiments, the one or more lipid markers comprise a single marker. In certain embodiments, the one or more lipid markers comprise a plurality of markers. In certain embodiments, the one or more lipid markers comprise 2 or more markers, 3 or more markers, 4 or more markers, or 5 or more markers. In certain embodiments, the one or more lipid markers comprise at least 2 markers, at least 3 markers, at least 4 markers, or at least 5 markers. In certain embodiments, the one or more lipid markers comprise a combination of markers.

In certain embodiments, the one or more lipid markers comprise at least two markers.

In certain embodiments, the one or more lipid markers are detected at the same time and/or from the same sample. For example, mass spectrometric analysis may be used to detect a variety of lipid markers in a sample simultaneously.

In certain embodiments, the method comprises detecting one or more lipid markers and one or more other non-lipid markers. In certain embodiments, the method comprises detecting one or more additional markers in conjunction with the one or more lipid markers. The markers can be detected at the same time or at different times, and can utilise the same method of detection or a different method of detection. Examples of non-lipid markers included PAPP-A, β-hCG, AFP, uE3, and Inhibin.

For example, in the case of trisomy 21 and 18 screening, additional markers include β-hCG, PAPP-A, AFP, uE3, and Inhibin A. Methods for screening using such markers are known in the art.

For example, decreased levels of PAPP-A before the 14th week of gestation are typically associated with an increased risk for trisomy 21 and trisomy 18. Increased levels of β-hCG are typically associated with an increased risk of trisomy 21 Down syndrome.

In certain embodiments, the one or more lipid markers have a molecular weight in the range from 100 to 3000, 100 to 2000, 100 to 1000, 100 to 500, 100 to 200, 200 to 3000, 200 to 2000, 200 to 1000, 200 to 500, 500 to 3000, 500 to 2000, and 500 to 1000 Daltons. In certain embodiments, the one or more markers have a size in the range of 3000 Daltons or less, 2000 Daltons or less 1000 Daltons or less, 500 Daltons or less, 400 Daltons or less, 300 Daltons or less, or 200 Daltons or less. Other ranges or sizes are contemplated.

In certain embodiments, the one or more markers have a molecular weight in the range from 100 to 3000 Daltons. In certain embodiments, the one or more markers have a molecular weight in the range from 200 to 3000 Daltons.

In certain embodiments, the one or more lipid markers have a molecular weight of 3000 Daltons or less, 2000 Daltons or less, 1500 Daltons or less, 1400 Daltons or less, 1300 Daltons or less, 1200 Daltons or less, 1100 Daltons or less, 1000 Daltons or less, 900 Daltons or less, 800 Daltons or less, 700 Daltons or less, 600 Daltons or 500 Daltons or less, 400 Daltons or less, 300 Daltons or less, or 200 Daltons or less. Other sizes are contemplated.

In certain embodiments, the one or more lipid markers have a molecular weight in the range from 100 to 3000, 100 to 2000, 100 to 1000, 100 to 500, 100 to 200, 200 to 3000, 200 to 2000, 200 to 1000, 200 to 500, 500 to 2000, and 500 to 1000 Daltons. Other ranges are contemplated.

In certain embodiments, the one or more lipid markers have a molecular weight in the range 100 to 3000, 100 to 2000, 100 to 1000, 100 to 500, 100 to 300, 100 to 200, 200 to 3000, 200 to 2000, 200 to 1000, 200 to 500, 200 to 300, 300 to 3000, 300 to 2000, 300 to 1000, 300 to 500, 500 to 3000, 500 to 2000, and 500 to 1000 Daltons. Other ranges are contemplated.

In certain embodiments, the one or more lipid markers have a molecular weight in the range from 300 to 1500, 300 to 1400, 300 to 1300, 300 to 1200, 300 to 1100, 300 to 1000, 300 to 900, 300 to 800, 300 to 700, 300 to 600, 300 to 500, 300 to 400, 400 to 1500, 400 to 1400, 400 to 1300, 400 to 1200, 400 to 1100, 400 to 1000, 400 to 900, 400 to 800, 400 to 700, 400 to 600, 400 to 500, 500 to 1500, 500 to 1400, 500 to 1300, 500 to 1200, 500 to 1100, 500 to 1000, 500 to 900, 500 to 800, 500 to 700, 500 to 600, 600 to 1500, 600 to 1400, 600 to 1300, 600 to 1200, 600 to 1100, 600 to 1000, 600 to 900, 600 to 800, 600 to 700, 700 to 1500, 700 to 1400, 700 to 1300, 700 to 1200, 700 to 1100, 700 to 1000, 700 to 900, 700 to 800, 800 to 1500, 800 to 1400, 800 to 1300, 800 to 1200, 800 to 1100, 800 to 1000, 800 to 900, 900 to 1500, 900 to 1400, 900 to 1300, 900 to 1200, 900 to 1100, 900 to 1000, 1000 to 1500, 1000 to 1400, 1000 to 1300, 1000 to 1200, 1000 to 1100, 1100 to 1500, 1100 to 1400, 1100 to 1300, 1100 to 1200, 1200 to 1500, 1200 to 1400, 1200 to 1300, 1300 to 1500, 1300 to 1400, and 1400 to 1500 Daltons. Other ranges are contemplated.

The detecting of the one or more lipid markers may be accomplished by one or more suitable methods know in the art. Examples of detection methods include mass spectrometric methods, immunological methods, electrophoretic methods, binding-partner methods, chromatographic methods, chromogenic methods, chemical reaction methods, absorbance methods, spectrographic methods, affinity methods and combinations thereof. For example, detection and/or analysis of lipids is as described in Lipid Analysis in Oils and Fats (1997) edited by R. J. Hamilton, Springer Science & Business Media.

For example, methods for detecting lipid markers include mass spectrometry, and/or high pressure liquid chromatography.

In certain embodiments, the method comprises mass spectrometry to detect the one or more lipid markers. In certain embodiments, the method comprises detecting the one or more lipid markers by mass spectrometry. In certain embodiments, the mass spectrometry comprises using positive ion mass spectrometry. In certain embodiments the mass spectrometry comprises using negative ion mass spectrometry.

In certain embodiments, the detecting of the one or more lipid markers comprises a mass determination. In certain embodiments, the detecting comprises mass spectrometric analysis. Examples of mass spectrometric analysis include electrospray ionization, matrix-assisted laser desorption and ionization, and time-of-flight mass spectrometry, atmospheric chemical ionization, atmospheric photo spray ionization, liquid extraction surface analysis, desorption electrospray ionization, triple quadruple mass spectrometry, quadruple ion trap mass spectrometry, differential mobility mass spectrometry. For example, mass spectrometric detection and analysis of lipids is generally as described in Robert C. Murphy "Mass Spectrometry of Lipids" Springer-Verlag New York, LLC (1993) and Isaac G, et al (2007) "New mass-spectrometry-based strategies for lipids" Genet Eng (N Y). 28:129-57.

For example, mass spectrometric analysis to determine the risk of a fetal trisomy typically involves one or more of the following steps: drawing a biological sample from the subject; processing the biological sample to form a processed sample in a manner such that it can be analysed in a mass spectrometer; analysing the processed sample in a mass spectrometer to identify and/or quantify one or more markers associated with the presence and/or absence of a fetal trisomy or indicative of the likelihood or risk of a fetal trisomy; comparing the level of the marker(s) in the female subject to a level of the marker(s) in a population of pregnant females who were determined to have a fetal trisomy and/or a population of pregnant females who were determined to not have a fetal trisomy; and determining the likelihood or risk of a pregnant female having or not having a fetus with a fetal trisomy.

Certain embodiments of the present disclosure provide use of a mass spectrometer to determine whether a lipid marker associated with the presence and/or absence of a fetal trisomy, and/or a lipid marker indicative of the likelihood or risk of a fetal trisomy, is present or not present in a biological sample of a female.

In certain embodiments, the method comprises determining the presence and/or level of the one or more lipid markers. In certain embodiments, the detecting of the one or more lipid markers comprises detecting the presence and/or level of the one or more lipid markers. For example, the concentration of the one or more lipid markers may be used to make an assessment of the risk of a trisomy, and/or the presence of the one or more lipid markers at a certain abundance may be used to make an assessment of the risk of a trisomy.

In certain embodiments, the method comprises determination of the mass of the one or more lipid markers and/or determination of the mass of one or more fragments of the one or more lipid markers.

In certain embodiments, the method comprises detecting the one or more lipid markers by mass spectrometry.

In certain embodiments, the method comprises detecting one or more lipid markers with a molecular weight in the range from 100 to 3000, 100 to 2000, 100 to 1000, 100 to 500, 100 to 200, 200 to 3000, 200 to 2000, 200 to 1000, 200 to 500, 500 to 2000, and 500 to 1000 Daltons. Other ranges are contemplated.

In certain embodiments, the method comprises detecting one or more lipid markers with a molecular weight in the range from 100 to 3000, 100 to 2000, 100 to 1000, 100 to 500, 100 to 300, 100 to 200, 200 to 3000, 200 to 2000, 200 to 1000, 200 to 500, 200 to 300, 300 to 3000, 300 to 2000, 300 to 1000, 300 to 500, 500 to 3000, 500 to 2000, and 500 to 1000 Daltons. Other ranges are contemplated.

In certain embodiments, the method comprises detecting one or more lipid markers with a molecular weight in the range from 300 to 1500, 300 to 1400, 300 to 1300, 300 to 1200, 300 to 1100, 300 to 1000, 300 to 900, 300 to 800, 300 to 700, 300 to 600, 300 to 500, 300 to 400, 400 to 1500, 400 to 1400, 400 to 1300, 400 to 1200, 400 to 1100, 400 to 1000, 400 to 900, 400 to 800, 400 to 700, 400 to 600, 400 to 500, 500 to 1500, 500 to 1400, 500 to 1300, 500 to 1200, 500 to 1100, 500 to 1000, 500 to 900, 500 to 800, 500 to 700, 500 to 600, 600 to 1500, 600 to 1400, 600 to 1300, 600 to 1200, 600 to 1100, 600 to 1000, 600 to 900, 600 to 800, 600 to 700, 700 to 1500, 700 to 1400, 700 to 1300, 700 to 1200, 700 to 1100, 700 to 1000, 700 to 900, 700 to 800, 800 to 1500, 800 to 1400, 800 to 1300, 800 to 1200, 800 to 1100, 800 to 1000, 800 to 900, 900 to 1500, 900 to 1400, 900 to 1300, 900 to 1200, 900 to 1100, 900 to 1000, 1000 to 1500, 1000 to 1400, 1000 to 1300, 1000 to 1200, 1000 to 1100, 1100 to 1500, 1100 to 1400, 1100 to 1300, 1100 to 1200, 1200 to 1500, 1200 to 1400, 1200 to 1300, 1300 to 1500, 1300 to 1400, and 1400 to 1500 Daltons. Other ranges are contemplated.

In certain embodiments, the method comprises detecting one or more lipid markers with a size of 3000 Daltons or less, 2000 Daltons or less, 1500 Daltons or less, 1400 Daltons or less, 1300 Daltons or less, 1200 Daltons or less, 1100 Daltons or less, 1000 Daltons or less, 900 Daltons or less, 800 Daltons or less, 700 Daltons or less, 600 Daltons or 500 Daltons or less, 400 Daltons or less, 300 Daltons or less, or 200 Daltons or less. Other sizes are contemplated.

In certain embodiments, the one or more lipid markers have a mass to charge ratio m/z of 3000 or less. In certain embodiments, the one or more lipid markers have a mass to charge ratio m/z of 2000 or less. In certain embodiments, the one or more lipid markers have a mass to charge ratio m/z of 1000 or less. In certain embodiments, the one or more lipid markers have a mass to charge ratio m/z of 1700 or less.

In certain embodiments, the one or more lipid markers have a mass to charge ratio m/z of 3000 Daltons or less, 2000 Daltons or less, 1500 Daltons or less, 1400 Daltons or less, 1300 Daltons or less, 1200 Daltons or less, 1100 Daltons or less, 1000 Daltons or less, 900 Daltons or less, 800 Daltons or less, 700 Daltons or less, 600 Daltons or 500 Daltons or less, 400 Daltons or less, 300 Daltons or less, or 200 Daltons or less. Other sizes are contemplated.

In certain embodiments, the one or more lipid markers have a mass to charge ratio m/z in the range from 100 to 3000, 100 to 2000, 100 to 1000, 100 to 500, 100 to 200, 200 to 3000, 200 to 2000, 200 to 1000, 200 to 500, 500 to 2000, and 500 to 1000 Daltons. Other ranges are contemplated.

In certain embodiments, the one or more lipid markers have a mass to charge ratio m/z in the range from 100 to 3000, 100 to 2000, 100 to 1000, 100 to 500, 100 to 300, 100 to 200, 200 to 3000, 200 to 2000, 200 to 1000, 200 to 500, 200 to 300, 300 to 3000, 300 to 2000, 300 to 1000, 300 to 500, 500 to 3000, 500 to 2000, and 500 to 1000 Daltons. Other ranges are contemplated.

In certain embodiments, the one or more lipid markers have a mass to charge ratio m/z in the range from 300 to 1500, 300 to 1400, 300 to 1300, 300 to 1200, 300 to 1100, 300 to 1000, 300 to 900, 300 to 800, 300 to 700, 300 to 600, 300 to 500, 300 to 400, 400 to 1500, 400 to 1400, 400 to 1300, 400 to 1200, 400 to 1100, 400 to 1000, 400 to 900, 400 to 800, 400 to 700, 400 to 600, 400 to 500, 500 to 1500, 500 to 1400, 500 to 1300, 500 to 1200, 500 to 1100, 500 to 1000, 500 to 900, 500 to 800, 500 to 700, 500 to 600, 600 to 1500, 600 to 1400, 600 to 1300, 600 to 1200, 600 to 1100, 600 to 1000, 600 to 900, 600 to 800, 600 to 700, 700 to 1500, 700 to 1400, 700 to 1300, 700 to 1200, 700 to 1100, 700 to 1000, 700 to 900, 700 to 800, 800 to 1500, 800 to 1400, 800 to 1300, 800 to 1200, 800 to 1100, 800 to 1000, 800 to 900, 900 to 1500, 900 to 1400, 900 to 1300, 900 to 1200, 900 to 1100, 900 to 1000, 1000 to 1500, 1000 to 1400, 1000 to 1300, 1000 to 1200, 1000 to 1100, 1100 to 1500, 1100 to 1400, 1100 to 1300, 1100 to 1200, 1200 to 1500, 1200 to 1400, 1200 to 1300, 1300 to 1500, 1300 to 1400, and 1400 to 1500 Daltons. Other ranges are contemplated.

In certain embodiments, a lipid marker has a mass of tolerance of +/−5 ppm, +/−10 ppm, +/−20 ppm, +/−50 ppm, or +/−100 ppm.

In certain embodiments, the one or more lipid markers comprise a lipid with one or more ions with the following assigned m/z: 703.5580, 369.3491, 367.3312, 680.5953; 687.5651, 445.3648, 445.3633, 727.5567, 429.3706, 1202.3250, 431.3875, 429.3726, 844.6007, 688.5950, 890.7703, 1276.3440, 711.5619, 1128.3140, 670.6080, and/or one or more of the aforementioned lipid markers with a mass tolerance of +/−20 ppm, and/or a substantially similar m/z and/or retention time.

In certain embodiments, the one or more lipid markers comprise a lipid with one or more ions with the following assigned m/z: 340.3576, 355.2511, 363.2531, 390.7783, 399.3453, 404.7929, 407.2269, 408.3136, 427.3771, 429.2121, 447.3448, 447.3460, 461.3620, 469.3597, 471.4063, 473.3184, 478.3545, 481.3239; 489.4134, 506.4412, 530.5135, 544.5071, 551.5172, 555.4646, 558.5448, 568.4784, 579.4305, 603.4949, 604.5660, 607.5640, 618.5444, 626.4976, 640.5345, 640.5699, 647.5577, 676.4879, 684.5594, 700.5542, 728.5875, 740.5176, 744.5807, 772.6135, 780.5458, 788.6118, 798.5637, 817.5510, 816.6401, 820.5947, 826.5947, 832.6303, 834.5978, 850.5523, 860.6632, 864.5363, 876.6591, 902.5855, 904.6889, 904.6932, 920.6888, 928.5873, 948.7143, 964.7115, 992.7408, 1008.7339, 1036.7696, 1052.7680, 1078.9686, 670.6080, and/or one or more of the aforementioned lipid markers with a mass tolerance of +/−20 ppm, and/or a substantially similar m/z.

Figure 1:
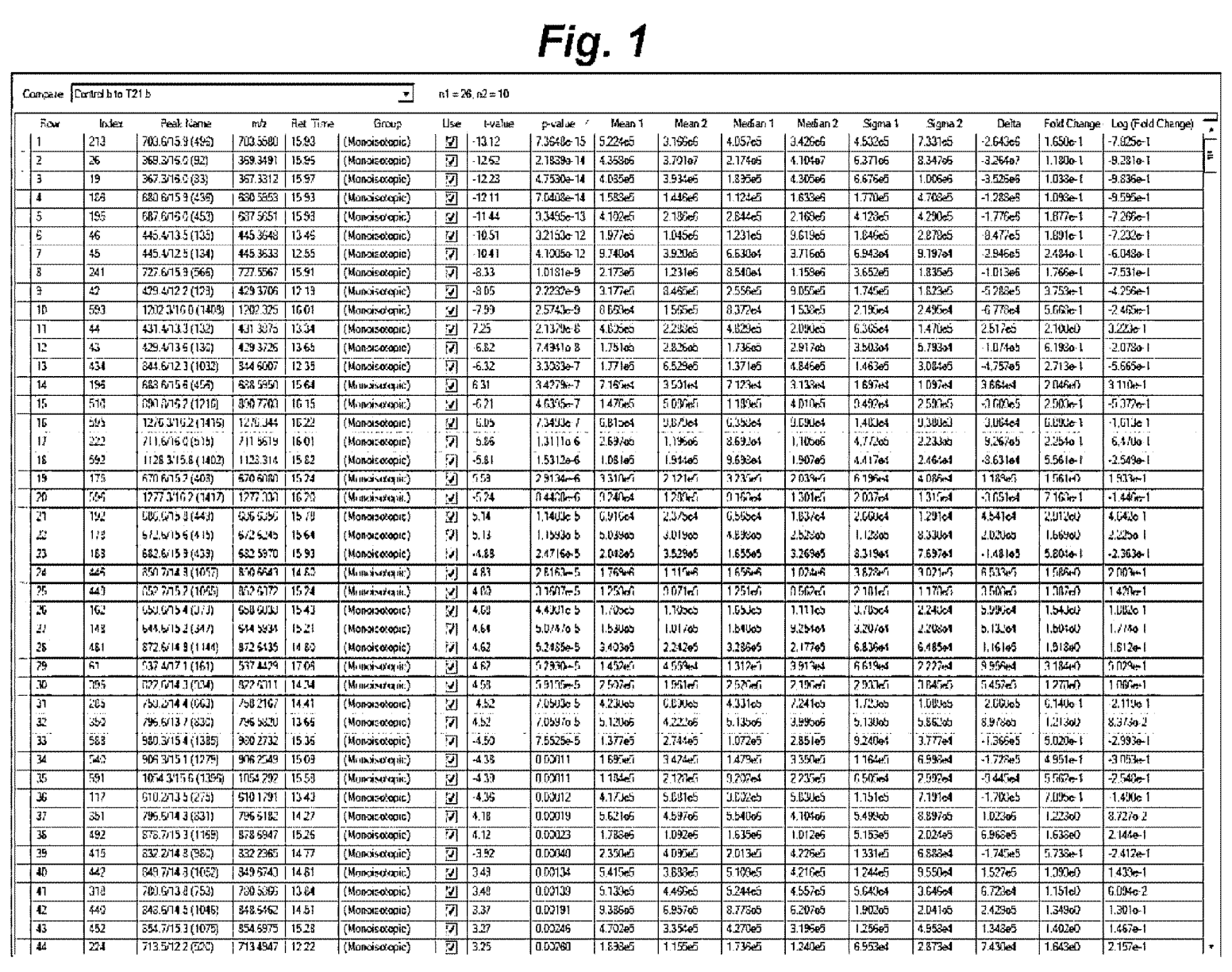

In certain embodiments, the one or more lipid markers comprise a lipid with one or more ions with the assigned m/z and/or retention times as provided in FIG. 1, and/or a substantially similar m/z and/or retention time, and/or a lipid with one or more ions with an assigned m/z as provided in Table 2 or 3 and/or a substantially similar m/z.

Certain embodiments of the present disclosure provide use of a mass spectrometer to detect one or more lipid markers from a biological sample of a pregnant female subject, wherein the one or more lipid markers are indicative of the risk of a fetal trisomy in a pregnant female.

Certain embodiments of the present disclosure provide a mass spectrographic method of screening for a fetal trisomy in a pregnant female subject.

Certain embodiments of the present disclosure provide a mass spectrographic method of screening for a fetal trisomy in a pregnant female subject, the method comprising:
  processing a biological sample from the subject to allow detection of lipid markers;
  detecting by mass spectrometry one or more lipid markers in the processed sample indicative of the risk of a fetal trisomy in the subject; and
  determining the risk of a fetal trisomy in the pregnant female subject on the basis of the one or more lipid markers detected.

Certain embodiments of the present disclosure provide a mass spectrographic method of screening for a fetal trisomy in a pregnant female subject, the method comprising:
  processing a biological sample from the subject to allow detection of lipid markers;
  detecting by mass spectrometry one or more lipid markers in the processed sample indicative of the risk of a fetal trisomy in the subject; and
  determining the presence or absence of a fetal trisomy in the pregnant female subject on the basis of the one or more lipid markers detected.

In certain embodiments, the one or more lipid markers comprise one or more fatty acid or fatty acyl groups.

Examples of fatty acids include straight-chain saturated fatty acids, branched-chain fatty acids, fatty acids with one or more double bonds and/or acetylenic bonds, heteroatom fatty acids, cyclic fatty acids, thio fatty acids, octadecanoids, eicosanoids, docosanoids, fatty acid esters such as wax monoesters, diesters and lactones, fatty alcohols, fatty aldehydes, fatty amides, and fatty ethers.

In certain embodiments, the one or more lipid markers comprise one, two, three or four chain fatty acid groups. In certain embodiments, the one or more lipid markers comprise one, two, three or four long chain fatty acid groups.

In certain embodiments, the one or more lipid markers comprise one or more long chain fatty acid groups. In certain embodiments, the one or more lipid markers comprise two long chain fatty acid groups.

In certain embodiments, the one or more lipid markers comprise one or more long chain polyunsaturated fatty acid groups. In certain embodiments, the one or more lipid markers comprise two long polyunsaturated chain fatty acid groups.

In certain embodiments, the one or more long chain fatty acid groups comprise a long chain polyunsaturated fatty acid group.

In certain embodiments, the one or more lipid markers comprise one or more long chain fatty acid groups with a chain length of 14 to 30 carbon atoms.

In certain embodiments, the one or more lipid markers comprise one or more long chain fatty acid groups with a chain length of 16 to 22 carbon atoms.

In certain embodiments, the one or more lipid markers comprise one or more of a phoshopholipid, a glycerolipid, a glycerophospholipid, a sphingolipid, a ceramide, a sterol, a glycosphingolipid, a dolicol, a lysolipid, a fatty acid, a triacylglyceride, a diacylglycerides, a monacylglycerides, an isoprenoid, a prostanoid, an eicosanoid, a sterol derivatives, a prenol lipid, a saccharolipid, a saturated fatty acid, a long chain saturated fatty acid, an unsaturated fatty acid, a polyunsaturated fatty acid, a long chain polyunsaturated fatty acid, a cholesterol and isomers thereof, a dehydrocholesterol and isomers thereof, a cholesterol ester and isomers thereof, a dehydrocholesterol ester and isomers thereof, a lyso derivative of any of the aforementioned lipid markers and/or a fragment and/or ion of any of the aforementioned lipid markers.

In certain embodiments, the one or more lipid markers comprise one or more phospholipids.

In certain embodiments, the one or more lipid markers comprise a cholesterol and isomers thereof, a dehydrocholesterol and isomers thereof, a cholesterol ester and isomers thereof, a dehydrocholesterol ester and isomers thereof, and/or a fragment and/or ion of any of the aforementioned lipids. In certain embodiments, the one or more lipid markers comprise one or more of a cholesterol ester of C22:3, a cholesterol ester of dihydroxylated C20:5, cholesterol, and 7-dehydrocholesterol.

In certain embodiments, the one or more lipid markers comprise one or more ions of a lipid with the following assigned m/z and/or retention times:

| m/z | Ret. Time | m/z | Ret. Time |
| --- | --- | --- | --- |
| 703.5580 | 15.93 | 1202.325 | 16.01 |
| 369.3491 | 15.96 | 431.3875 | 13.34 |
| 367.3312 | 15.97 | 429.3726 | 13.65 |
| 680.5953 | 15.93 | 844.6007 | 12.35 |
| 687.5651 | 15.98 | 688.5950 | 15.64 |
| 445.3648 | 13.46 | 890.7703 | 16.15 |
| 445.3633 | 12.55 | 1276.3440 | 16.22 |
| 727.5567 | 15.91 | 711.5619 | 16.01 |
| 429.3706 | 12.19 | 1128.3140 | 15.82 |
| 1202.3250 | 16.01 | 670.6080 | 15.24 | and/or one or more of the aforementioned lipid markers with a mass tolerance of +/−20 ppm, and/or a substantially similar m/z and/or retention time, and/or a fragment and/or ion thereof.

In certain embodiments, the one or more lipid markers comprise a lipid with one or more ions with the assigned m/z and/or retention times as provided in FIG. 1, and/or a substantially similar m/z and/or retention time, and/or a fragment and/or ion thereof.

In certain embodiments, the one or more lipid markers comprise, for one or more of each of the assigned m/z and/or retention times described above or in FIG. 1, a cholesterol and isomers thereof, a dehydrocholesterol and isomers thereof, a cholesterol ester and isomers thereof, a dehydrocholesterol ester and isomers thereof, and/or a fragment and/or ion thereof.

In certain embodiments, the method comprises determining one or more characteristics of the one or more lipid markers. Examples of one or more characteristics include the presence and/or level of a marker, a modification of a marker, localisation of a marker, or association of a marker with another molecule, the pattern (or profile) of a lipid under mass spectrometric analysis, the fragmentation pattern of a lipid under mass spectrometric analysis, concentration, and abundance. Other types of characteristics are contemplated.

In certain embodiments, the one or more characteristics comprise the presence and/or level of the one or more lipid markers.

In certain embodiments, the one or more characteristics are indicative of the presence or absence of the fetal trisomy in the subject. In certain embodiments, the one or more characteristics are indicative of the likelihood and/or risk of a fetal trisomy in a subject. For example, an altered level and/or concentration of the one or more markers may be indicative of the presence or absence of a fetal trisomy in the subject, and/or indicative of the likelihood and/or risk of a fetal trisomy in a subject In certain embodiments, the detecting of the one or more lipid markers comprises detecting the presence and/or level of the one or more lipid markers, and/or fragments and/or ions thereof.

In certain embodiments, the level of the one or more lipid markers is altered. In certain embodiments, the level of one or more of the markers is increased. In certain embodiments, the level of one or more of the markers is decreased.

In certain embodiments, an increased level of one or more of the lipid markers is indicative of an increased risk of a fetal trisomy. In certain embodiments, a decreased level of one or more of the lipid markers is indicative of an increased risk of a fetal trisomy. In certain embodiments, an increased level of one or more of the lipid markers is indicative of a decreased risk of a fetal trisomy. In certain embodiments, a decreased level of one or more of the lipid markers is indicative of a decreased risk of a fetal trisomy.

In certain embodiments, an increased level of one or more lipid marks in conjunction with a decreased level of one or more other lipid markers is indicative of an increased risk of a fetal trisomy. In certain embodiments, an increased level of one or more lipid marks in conjunction with a decreased level of one or more other lipid markers is indicative of a decreased risk of a fetal trisomy.

In certain embodiments, an increased level of one or more of the lipid markers is indicative of the presence of a fetal trisomy. In certain embodiments, a decreased level of one or more of the lipid markers is indicative of the presence of a fetal trisomy. In certain embodiments, an increased level of one or more of the lipid markers is indicative of the absence of a fetal trisomy. In certain embodiments, a decreased level of one or more of the lipid markers is indicative of the absence a fetal trisomy.

In certain embodiments, an increased level of one or more of the lipid markers and a decreased level of one or more other lipid markers is indicative of the presence of a fetal trisomy. In certain embodiments, an increased level of one or more of the lipid markers and a decreased level of one or more other lipid markers is indicative of the absence of a fetal trisomy.

In certain embodiments, the altered level of the one or more markers is altered by 1.1 fold or more, 1.2 fold or more, 1.3 fold or more, 1.4 fold or more, 1.5 fold or more, 1.6 fold or more, 1.7 fold or more, 1.8 fold or more, 1.9 fold or more, 2 fold or more, 3 fold or more, 4 fold or more, 5 fold or more, 10 fold or more, 20 fold or more, 50 fold or more, or 100 fold or more. The alteration may be upregulation and/or down-regulation of the one or more markers. For example, the level of the one or markers may be increased by 2 fold or more, 3 fold or more, 4 fold or more, 5 fold or more, 10 fold or more, 20 fold or more, 50 fold or more, or 100 fold, or decreased by 2 fold or more, 3 fold or more, 4 fold or more, 5 fold or more, 10 fold or more, 20 fold or more, 50 fold or more, or 100 fold or more.

In certain embodiments, the method comprises comparing one or more characteristics of the one or more markers with other markers or characteristics of other markers. In certain embodiments, the method comprises comparing one or more characteristics of the one or more markers with a reference set of markers or characteristics of markers. Typically, such markers are markers that are differentially present between a pregnant female subject having a fetal trisomy and a pregnant female subject without a fetal trisomy.

In certain embodiments, the method comprises comparing one or more characteristics of the one or more lipid markers with one or more of: (i) one or more characteristics of one or more other markers known to be indicative of an increased risk of a fetal trisomy; (ii) one or more characteristics of one or more other markers known to be indicative of a decreased risk of a fetal trisomy; (iii) one or more characteristics of one or more other markers known to be indicative of the presence of a fetus trisomy; and (iv) one or more characteristics of one or more other markers known to be indicative of the absence of a fetal trisomy. As discussed herein, in certain embodiments the one or more characteristics comprise the presence and/or level of one or more markers. Other markers that are indicative of the risk, presence or absence of a fetal trisomy are known or may be identified.

In certain embodiments, the method comprises comparing one or more of the lipid markers with one or more following: (i) one or more markers known to be indicative of an increased risk of a fetal trisomy; (ii) one or more markers known to be indicative of a decreased risk of a fetal trisomy; (iii) one or more markers known to be indicative of the presence of a fetus with a fetal trisomy in a pregnant female subject; and (iv) one or more markers known to be indicative of a fetus without a fetal trisomy in a pregnant female subject.

In certain embodiments, the method comprises comparing one or more of the lipid markers with one or more following: (i) one or more markers known to be indicative of an increased risk of a fetal trisomy; (ii) one or more markers known to be indicative of a decreased risk of a fetal trisomy; (iii) one or more markers known to be indicative of the presence of a fetal trisomy; (iv) one or more markers known to be indicative of the absence of a fetal trisomy.

In certain embodiments, the method comprises comparing the one or more lipid markers or characteristics of the one or more lipid markers with one or more control markers and/or one or more reference markers. For example, control markers may be used to normalise the level of markers across different samples or for comparative purposes. In certain embodiments, the one or more control markers comprise one or more markers from a subject with an unaffected pregnancy and/or one or more markers from a subject with an affected pregnancy.

In certain embodiments, one or more reference markers may be used, for example to verify size and/or detection of markers, and/or to monitor processing of samples. In certain embodiments, the one or more reference markers are detectably labelled. For example, the one or more reference markers may be labelled, such as being isotopically labelled.

In certain embodiments, the method comprises using a lipid as a reference marker to detect the one or more lipid markers by mass spectrometry. In certain embodiments, the method comprises using an isotopically labelled lipid as a reference marker to quantify relative amounts of the one or more lipid markers.

In certain embodiments, the method comprises determining the ratio of one or more markers to one or more other markers. For example, the ratio of one or more lipid markers to one or more other lipid markers may be determined, and be indicative of the risk of a fetal trisomy, and/or the ratio of one or more lipid markers to one or more non-lipid markers may be determined, and be indicative of the risk of a fetal trisomy.

In certain embodiments, the method comprises detecting the one or more lipid markers in the subject in the first trimester of pregnancy. In certain embodiments, the method comprises detecting the one or more markers in the subject in the second trimester of pregnancy.

In certain embodiments, the method comprises obtaining a biological sample from the subject. The term "sample" refers to a sample obtained from a subject, or any derivative, extract, concentrate, mixture, or otherwise processed form thereof.

Methods for obtaining biological samples are known in the art. Examples of biological samples include biological fluids, blood samples, plasma samples, serum samples, urine samples, tear samples, saliva samples, swab samples, hair samples, skin samples, dried blood samples, dried samples on a matrix, a biopsy, and fecal samples. Methods for collecting biological samples are known in the art. For example, blood samples may be collected using standard techniques such as drawing blood into a collection tube, pin-prick followed by absorption onto filter paper (eg Guthrie card), and devices that withdraw blood using a vacuum (eg Hemolink, Tasso Inc.).

In certain embodiments, the biological sample is a biological fluid. In certain embodiments, the biological fluid comprises one or more of blood, plasma and serum. In certain embodiments, the biological fluid comprises one or more of maternal blood, maternal plasma and maternal serum.

In certain embodiments, the one or more lipid markers comprise one or more markers present in a biological fluid. In certain embodiments, the one or more lipid markers comprise one or more blood markers, plasma markers and/or serum markers.

In certain embodiments, the method comprises obtaining a biological sample from the subject in the first trimester of pregnancy. In certain embodiments, the method comprises obtaining a biological sample from the subject in the second trimester of pregnancy.

In certain embodiments, the method comprises processing the biological sample to allow detection of the one or more markers. In certain embodiments, the method comprises processing a biological sample obtained from the subject and detecting the one or more markers.

Certain embodiments of the present disclosure provide a method of screening for a fetal trisomy in a pregnant female subject, the method comprising:
  processing a biological sample from the subject to allow detection of lipid markers;
  detecting one or more lipid markers in the processed sample indicative of the risk of a fetal trisomy in the subject; and determining the risk of a fetal trisomy in the pregnant female subject on the basis of the one or more lipid markers detected.

Certain embodiments of the present disclosure provide a method of screening for a fetal trisomy in a pregnant female subject, the method comprising:

processing a biological sample from the subject to allow detection of lipid markers;

detecting one or more lipid markers in the processed sample indicative of the risk of a fetal trisomy in the subject; and determining the presence or absence of a fetal trisomy in the pregnant female subject on the basis of the one or more lipid markers detected.

Certain embodiments of the present disclosure provide a method of screening for a fetal trisomy in a pregnant female subject, the method comprising:

processing a biological sample from the subject to allow detection of lipid markers by mass spectrometry;

detecting by mass spectrometry one or more lipid markers in the processed sample indicative of the risk of a fetal trisomy in the subject; and determining the risk of a fetal trisomy in the pregnant female subject on the basis of the one or more lipid markers detected.

Certain embodiments of the present disclosure provide a method of screening for a fetal trisomy in a pregnant female subject, the method comprising:

processing a biological sample from the subject to allow detection of lipid markers by mass spectrometry;

detecting by mass spectrometry one or more lipid markers in the processed sample indicative of the risk of a fetal trisomy in the subject; and determining the presence or absence of a fetal trisomy in the pregnant female subject on the basis of the one or more lipid markers detected.

In certain embodiments, the method comprises processing the biological sample to allow detection of the one or more lipid markers in the biological sample. For example, to allow detection of lipid markers, the sample may be exposed to a substantially organic solvent(s) to partition molecules into organic/non-organic fractions/polar and non-polar fractions. Examples of solvents include methanol, butanol, propanol, acetonitrile, chloroform and mixtures thereof (including mixtures with water-based solvents) and extraction techniques such as the Folch technique (Folch J et al (1957) *J Biol Chem.* 226(1):497-509.). Samples may be further processed if required to allow detection of one or more markers by the desired method.

In certain embodiments, the method comprises exposing the biological sample, and/or a processed form, an extract, a derivative, a component or a fraction thereof to a substantially organic solvent and isolating the organic fraction.

In certain embodiments, a reference lipid is added prior to and/or after extraction with an organic solvent. In certain embodiments, an isotopically labelled lipid is added prior to and/or after extraction with an organic solvent. In certain embodiments, the isotopically labelled lipid is an isotopically labelled form of a naturally occurring lipid.

In certain embodiments, the method comprises exposing the biological sample (and/or an extract, derivative, component or fraction thereof) to a solvent and isolating the organic fraction. In certain embodiments, the method comprises exposing the biological sample (and/or an extract, derivative, component or fraction thereof) to a substantially non-polar solvent and isolating the non-polar fraction. In certain embodiments, the method comprises processing the biological sample with a substantially non-polar solvent. In certain embodiments, the method comprises processing the biological sample with an organic solvent. Buffers, for example to maintain pH, can also be added such as for example ammonium hydroxide or ammonium bicarbonate.

In certain embodiments, method comprises spiking the biological sample (and/or an extract, derivative, component or fraction thereof) with a detectable reference compound. For example, the detectable reference compound may be a single or mixture of isotopically labelled, radioactively labelled, or fluorescently labelled or a chemical analogue. Other forms of labelling are contemplated. Derivatives of the biological sample or parts thereof to enhance signal detection or to simplify isomer or isobaric complications are contemplated.

In certain embodiments, the method comprises a chromatographic separation step. In certain embodiments, the method comprises a liquid chromatographic separation step, such as HPLC.

In certain embodiments, for mass spectrometric analysis, the method comprises ionising a sample, sorting and separating the resultant ions according to their mass and charge, and measuring the ions. In certain embodiments, the method comprises use of liquid chromatography mass spectrometry (eg HPLC-MS).

In certain embodiments, the method comprises using a computer processor means to process data associated with the presence and/or level of the one or more lipid markers to generate or determine a likelihood and/or risk of the presence or absence of a fetal trisomy.

In certain embodiments, the generating or determining of the likelihood and/or risk comprises a multiple of mean analysis of the one or more of lipid markers to determine/generate a likelihood ratio for the risk. Other methods of determining likelihood and/or risk are contemplated.

In certain embodiments, the method comprises transferring the data/information over the internet to a computer processing means.

In certain embodiments, the method comprises transferring data associated with the one or more characteristics over the internet to a computer processing means to generate a likelihood or risk of the a fetal trisomy occurring, such as the likelihood or risk of the presence or absence of a fetal trisomy.

For example, web-based statistical software can be used to assesses the risk of a fetal trisomy and provide a probability of risk of a fetal trisomy occurring.

In certain embodiments, the method comprises processing the data/information to classify the risk in the subject as having increased risk, a high risk, a moderate risk, a low risk, a normal risk or a decreased risk. In certain embodiments, the method comprises processing the data/information to identity the presence or absence of a fetal trisomy. In certain embodiments, the method comprises processing the data/information to exclude the presence of a fetal trisomy.

Computer processing means are known in the art. Method for sending and/or receiving data/information are known in the art.

Certain embodiments of the present disclosure provide a system for determining the likelihood or risk of a fetal trisomy using a computer processor. Systems utilising computer processors are known in the art. Examples are as described herein.

Certain embodiments of the present disclosure provide a system for determining the risk of a fetal trisomy using a computer processor configured to process a method as described herein.

Certain embodiments of the present disclosure provide a method of screening for a fetal trisomy in a pregnant female subject, the method comprising:

detecting one or more lipid markers from the subject, wherein the one or more lipid markers is indicative of the risk of a fetal trisomy in the subject;

using a computer processor means to process data associated with the presence and/or level of the one or more lipid markers detected to generate a likelihood and/or risk of the presence or absence of a fetal trisomy; and determining the risk of a fetal trisomy in the pregnant female subject on the basis of the likelihood and/or risk generated.

Certain embodiments of the present disclosure provide a method of screening for a fetal trisomy in a pregnant female subject, the method comprising:

detecting one or more lipid markers from the subject, wherein the one or more lipid markers is indicative of the risk of a fetal trisomy in the subject;

using a computer processor means to process data associated with the presence and/or level of the one or more lipid markers detected to generate a likelihood and/or risk of the presence or absence of a fetal trisomy; and determining the presence or absence of a fetal trisomy in the pregnant female subject on the basis of the likelihood and/or risk generated.

Certain embodiments of the present disclosure provide a computer readable medium.

Certain embodiments of the present disclosure provide a computer-readable medium encoded with programming instructions executable by a computer processor means to allow the computer processor means to receive data associated with the presence and/or level of the one or more lipid markers indicative of the risk of a fetal trisomy in a subject and process the data to generate a likelihood and/or risk of the fetal trisomy in the subject.

Certain embodiments of the present disclosure provide a computer-readable medium encoded with programming instructions executable by a computer processor means to allow the computer processor means to receive data associated with the presence and/or level of the one or more lipid markers indicative of the risk of a fetal trisomy in a subject and process the data to generate a likelihood and/or risk of the presence or absence of a fetal trisomy in the subject.

Certain embodiments of the present disclosure provide a computer processor means comprising a computer-readable medium as described herein.

Certain embodiments of the present disclosure provide a mass spectrometer with a computer processor means comprising a computer-readable medium as described herein.

Certain embodiments of the present disclosure provide a method of identifying the presence or absence of a fetal trisomy in a pregnant female subject, using a method as described herein.

Fetal trisomies are as described herein. In certain embodiments, the fetal trisomy comprises a trisomy 21.

Lipid markers, and methods for detection of lipid markers, are as described herein. Methods for determining risk are as described herein.

Certain embodiments of the present disclosure provide a method of identifying the presence or absence of a fetal trisomy in a pregnant female subject, the method comprising:

detecting one or more lipid markers from the subject, wherein the one or more lipid markers is indicative of risk of a fetal trisomy in the subject; and identifying the presence or absence of a fetal trisomy in the pregnant female subject on the basis of the one or more lipid markers detected.

Certain embodiments of the present disclosure provide a method of identifying the presence or absence of a fetal trisomy in a pregnant female subject, the method comprising:

processing a biological sample from the subject to allow detection of lipid markers;

detecting one or more lipid markers in the processed sample indicative of the risk of a fetal trisomy in the subject; and identifying the presence or absence of a fetal trisomy in the pregnant female subject on the basis of the one or more lipid markers detected.

Certain embodiments of the present disclosure provide a method of identifying the presence or absence of a fetal trisomy in a pregnant female subject, the method comprising:

processing a biological sample from the subject to allow detection of lipid markers by mass spectrometry;

detecting by mass spectrometry one or more lipid markers in the processed sample indicative of the risk of a fetal trisomy in the subject; and identifying the presence or absence of a fetal trisomy in the pregnant female subject on the basis of the one or more lipid markers detected.

Certain embodiments of the present disclosure provide a method of identifying the presence or absence of a fetal trisomy in a pregnant female subject, the method comprising:

detecting one or more lipid markers from the subject, wherein the one or more lipid markers is indicative of the risk of a fetal trisomy in the subject; and using a computer processor means to process data associated with the presence and/or level of the one or more lipid markers to generate a likelihood and/or risk of the presence or absence of a fetal trisomy; and identifying the presence or absence of a fetal trisomy in the pregnant female subject on the basis of the likelihood and/or risk generated.

Certain embodiments of the present disclosure provide a method of identifying a pregnant female subject with an increased risk of carrying a fetal trisomy, using a method as described herein.

Certain embodiments of the present disclosure provide a method of identifying a pregnant female subject with an increased risk of carrying a fetal trisomy, the method comprising:

detecting one or more lipid markers from the subject, wherein the one or more lipid markers is indicative of an increased risk of a fetal trisomy in the subject; and identifying the subject as having an increased risk of carrying a fetal trisomy on the basis of the one or more lipid markers detected.

Certain embodiments of the present disclosure provide a method of determining the risk of a fetal trisomy, using a method as described herein.

Certain embodiments of the present disclosure provide a method of determining the risk of a pregnant female subject carrying a fetus with a trisomy, the method comprising:

detecting one or more lipid markers from the subject, wherein the one or more markers is indicative of the risk of a fetal trisomy in the subject; and determining the risk of the subject carrying a fetus with a trisomy on the basis of the one or more lipid markers detected.

Fetal trisomies are as described herein. In certain embodiments, the fetal trisomy comprises a trisomy 21.

Lipid markers, and methods for detection of lipid markers, are as described herein. Methods for determining risk are as described herein.

In certain embodiments, the determining of the risk comprises a computer processor means to process data associated with the presence and/or level of the one or more lipid markers. Computer processor means are as described herein.

In certain embodiments, the determining of the risk comprises a multiple of mean analysis of the one or more of lipid markers to determine a likelihood ratio for the risk.

Certain embodiments of the present disclosure provide a kit for performing a method as described herein.

In certain embodiments, the kit is a kit for mass spectrometric analysis.

In certain embodiments, the kit comprises one or more reagents and/or instructions for performing the methods, as described herein.

In certain embodiments, the kit comprises one or more reagents for processing a biological sample for analysis and/or one or more reagents for detecting one or more markers. Examples of biological samples and reagents are as described herein.

Examples of solvents for use in a kit include methanol, butanol, propanol, acetonitrile, chloroform and mixtures thereof (including mixtures with water-based solvents) and instructions for extraction techniques such as the Folch technique (Folch J et al (1957) *J Biol Chem.* 226(1):497-509.).

In certain embodiments, the kit comprises one or more isolated and/or detectably labelled markers.

The term "isolated" refers to an entity, such as a molecule, that is at least partially separated from other molecules. Examples of markers are as described herein. In certain embodiments, the one or more isolated and/or detectably labelled markers comprise one or more markers indicative of the presence and/or absence of a fetal trisomy. In certain embodiments, the one or more isolated and/or detectably labelled markers comprise one or more lipid markers. In certain embodiments, the one or more markers have a size in the range from 200 to 3000 Daltons. Other sizes are as described herein. In certain embodiments, the one or more markers have a mass to charge m/z ratio of 1700 or less when determined by mass spectrometry. Detectable labels are as described herein. Methods for detectably labelling are known. For example, the detectable label may comprise an antigen, an enzyme, a fluorophore, a quencher, a dye, an isotope, a radioactive isotope, or a luminescent moiety. In certain embodiments, the isolated and detectable labelled one or more markers comprise isotopic labelling (eg $^2$H, $^{18}$O, $^{13}$C or $^{15}$N).

In certain embodiments, the kit comprises one or more control markers. In certain embodiments, the one or more control markers comprise one or more markers from a subject with an unaffected pregnancy and/or one or more markers from a subject with an affected pregnancy.

In certain embodiments, the kit comprises a compound for spiking a biological sample. In certain embodiments, the compound comprises a nonphysiological compound, such as a lipid marker that is not present in blood.

In certain embodiments, the kit comprises one or more reference markers. For example, reference markers may be used to normalise the level of markers across different samples or for comparative purposes. In certain embodiments, reference markers may be used to verify size and/or detection of markers, and/or to monitor processing of samples. In certain embodiments, the one or more reference markers are detectably labelled. For example, the one or more reference markers may be labelled, such as being isotopically labelled, such as a deuterated lipid In certain embodiments, the kit comprises instructions for processing a biological sample and/or instructions for detecting the presence and/or level of one or more markers in a biological sample. In certain embodiments, the kit comprises instructions for processing a blood sample and/or instructions for detecting the presence and/or level of one or more lipid markers by mass spectrometric analysis.

In certain embodiments, the kit comprises instructions and/or information for use in determining whether one or more lipid markers are indicative of a fetus with a fetal trisomy or a fetus without a fetal trisomy. In certain embodiments, the information comprises data associated with the likelihood and/or risk of the presence or absence of a fetal trisomy.

In certain embodiments, the kit comprises a computer-readable medium encoded with programming instructions executable by a computer processor means to allow the computer processor means to receive data associated with one or more characteristics of one or more markers and process the data to generate a likelihood and/or risk of the presence or absence of a fetal trisomy.

In certain embodiments, the kit is used for screening for a fetal trisomy, to identify a fetal trisomy in a pregnant female subject, to identify the absence of a fetal trisomy in a pregnant female subject, to exclude an abnormal pregnancy in a pregnant female subject, to identify the likelihood and/or risk of a fetal trisomy, for prenatal screening, for prenatal testing and for prenatal diagnosis. Methods for performing the aforementioned uses of the kit are as described herein.

In certain embodiments, a kit is provided which comprises an analytical column and/or mobile phases useful in separating the markers. In certain embodiments the kit comprises standards of markers indicative of the presence or absence of the fetal trisomy in a subject.

Certain embodiments of the present disclosure provide a method for identifying one or more markers indicative of the risk of a fetal trisomy and/or indicative of the presence or absence of a fetal trisomy, as described herein.

Markers so identified are candidate markers, for example, for use in prenatal screening and prenatal diagnosis tests.

Fetal trisomies are as described herein. In certain embodiments, the fetal trisomy comprises a trisomy 21.

Lipid markers, and methods for detection of lipid markers, are as described herein. Methods for determining risk are as described herein.

Certain embodiments of the present disclosure provide a method of identifying one or more lipid markers indicative of the risk of a fetal trisomy, the method comprising:
  identifying one or more lipid markers which are differentially present between a pregnant female subject having a fetal trisomy and a pregnant female subject without a fetal trisomy; and
  identifying the one or more lipid markers as one or more lipid markers indicative of the risk of a fetal trisomy.

Certain embodiments of the present disclosure provide a method of identifying one or more lipid markers indicative of the presence or absence of a fetal trisomy, the method comprising:
  identifying one or more lipid markers which are differentially present between a pregnant female subject having a fetal trisomy and a pregnant female subject without a fetal trisomy; and identifying the one or more lipid markers as one or more lipid markers indicative of the presence or absence of a fetal trisomy.

Certain embodiments of the present disclosure provide a method of identifying one or more lipid markers indicative of the risk of a fetal trisomy, the method comprising identifying a plurality of lipid markers which in combination are indicative of the risk of a fetal trisomy.

In certain embodiments, the method comprises mass spectrometric analysis.

Certain embodiments of the present disclosure provide a method of identifying one or more lipid markers indicative of the risk of a fetal trisomy, the method comprising:

determining the presence of one or more lipid markers which are differentially present between a pregnant female subject having a fetal trisomy and a pregnant female subject without a fetal trisomy; and identifying the one or more lipid markers as one or more lipid markers indicative of the risk of a fetal trisomy.

Certain embodiments of the present disclosure provide a method of identifying one or more lipid markers indicative of the presence or absence a fetal trisomy, the method comprising:

determining the presence of one or more lipid markers which are differentially present between a pregnant female subject having a fetal trisomy and a pregnant female subject without a fetal trisomy; and identifying the one or more lipid markers as one or more lipid markers indicative of the presence or absence of a fetal trisomy.

Methods for determining whether a marker is differentially present are as described herein. In certain embodiments, the method comprises use of mass spectrometric analysis. Methods for comparing the presence and/or level of markers are as described herein.

Methods for identifying new candidate markers are also further substantially as herein described with reference to the Examples.

Certain embodiments of the present disclosure provide one or more lipid markers identified by a method as described herein. In certain embodiments, the one or more lipid markers are indicative of the presence or absence a fetal trisomy, or indicative of the risk of a fetal trisomy.

Certain exemplary embodiments are illustrated by some of the following examples. It is to be understood that the following description is for the purpose of describing particular embodiments only and is not intended to be limiting with respect to the above description.

Example 1—Metabolomics LC/MS Experimental Conditions

In one experiment, a set of trisomy 21 samples were distinguished from a control set as follows.

Serum samples from unaffected pregnancy and trisomy21 affected pregnancies were selected. These serum samples were extracted in duplicate according to the method of Folch (Folch J et al (1957) *J Biol Chem.* 226(1):497-509.). Serum (25 µL) plus 25 µL deionised water was extracted for 1 hour (minimum) with the addition of 1000 µL of chloroform: methanol (2:1, v/v) in 1.5 mL glass tubes fitted with Teflon lined screw caps and with vigorous mixing for the first 10 minutes. An internal standard was added at this stage (deuterated (d4) lyso-phosphatidylcholine, 0.125 µg/sample, Avanti Polar Lipids Inc.). Phase partitioning was induced, with the addition of 200 µL of 0.1M potassium chloride solution and vigorous mixing for 5 minutes, followed by centrifugation to aid in phase separation. The aqueous upper phase was removed to waste with gentle suction and minimal disturbance of the protein interface. The lipid containing organic solvent lower phase was removed to fresh glass autosampler tubes (fitted with 500 µL glass inserts) using glass Pasteur pipettes taking care to avoid the denatured protein at the interface. Contents of each tube were taken to dryness by evaporation of the organic solvent under a stream of nitrogen with the tubes maintained at a temperature of 40° C. The dried samples were reconstituted with 200 µL of chloroform:methanol (1:2, v/v) and stored at −20° centigrade ready for mass spectrometric analysis.

Lipid extracts were separated on an Agilent Technologies Inc. Poroshell 120, C18, 2.1×100 mm, 2.7 m column connected to a Shimadzu Nexera autosampler/liquid chromatograph system. A binary solvent system was used, in which mobile phase A consisted of methanol:water (3:1, v/v), 7.5 mM ammonium formate, and mobile phase B of 2-propanol, 7.5 mM ammonium formate. Solvents were of mass spectrometry grade. The HPLC program was: 0-5 min, 10% B; 5-15 min, a gradient from 10 to 80% B; 15-20 min, 80% B; 20-25 min a gradient from 80 to 10% B; 25-30 min, 10% B. Flow rate was 300 µL/minute. The sample tray was held at 4° C. and the column oven at 50° C. An AB SCIEX TripleTOF® 5600 QTOF (AB SCIEX, Concord, ON) with Analyst® TF 1.5.1 software was used to analyse the eluate from the UHPLC. The chromatographic solvent was directed into the ionisation source through the ESI probe.

Each sample was analysed in positive ion polarity using ESI ionisation. It should be noted that while the details provide here relate to positive ion analysis, for some lipids negative ion analysis is required as the lipids only ionise in negative ion polarity. Source parameters included nebulizing gases GS1 at 45, GS2 at 45 curtain gas at 30, spray voltage at 5400, declustering potential at 70 V, and at an ESI source operating temperature of 500° C. Experimental setting used was MS scans followed by MS/MS activation using the DDA criterial-3 charge state, exceeds 150 cps, exclude 3 seconds, exclude former ions after 2 repeats, exclude isotopes within 4 Da and dynamic background subtraction enabled. The scan range used was m/z 50-2000 using a 0.1 sec accumulation for TOF MS and then 0.05 sec accumulation for each TOF MS/MS. Collision energy for CID was 45.

Markerview Software v1.2.1.1 by Applied Biosystems (Framingham) was used to perform both t-tests and principal component analyses (PCA) to identify ions that are indicative of trisomy.

Markerview methods: Data from both control and affected samples were imported into Markerview using the File<import<LC/MS_data_from-wiff command using the following parameters:

| | |
|---|---|
| Period: | 1 |
| Experiment: | 1 |
| Min. Retention Time: | 10.00 min |
| Max. Retention Time: | 24.00 min |
| Subtraction Offset: | 10 scans |
| Subtraction Mult. Factor: | 1.3 |
| Noise Threshold: | 1000 |
| Min. Spectral Peak Width: | 20 ppm |
| Min. RT Peak Width: | 3 scans |
| Retention Time Tolerance: | 0.50 min |
| Mass Tolerance: | 20.0 ppm |
| Use Global Exclusion List: | False |
| Num Required Samples: | 18 |

-continued

| Max. Number of Peaks: | 5000 |
|---|---|
| Use Raw Data Area: | True |

Unaffected controls: SP 3, 7, 10, 13, 14, 17, 19, 22, 23, 27, 34, 37, 38. Trisomy 21: SP 1, 16, 26, 29, 33. t-tests were performed using the t-test option available and default settings.

The results from t-test of trisomy 21 and unaffected controls are shown in FIG. 1. The features differentiate trisomy 21 from normal unaffected pregnancy. P-values were found to be significant (<0.05) for up to 85 m/z ions. Fold changes calculated by mean 1 (unaffected) response/ mean 2 (trisomy 21 affected) response are also shown to both increase and decrease in some molecules. For example, some of the lipid markers were increased and in some cases by up to 8-fold (369.3/16.0 (index #26)), whereas other markers decreased by more than 2-fold, (688.6/15.6 (index #196)). These markers, either individually, in specific combinations, or collectively, provide a set of potential markers that can be used as a profile to identify a pregnancy with a trisomy.

FIG. 2 shows a selection of profile plots of individual m/z ions of the top 20 most significant individual m/z ions showing relative differences. FIG. 2 shows that the responses (intensity area under the curve) of individual m/z ions when plotted can differentiate between unaffected controls and samples from a trisomy [unaffected controls—SP 3, 7, 10, 13, 14, 17, 19, 22, 23, 27, 34, 37, 38; trisomy 21—SP 1, 16, 26, 29, 33]. These markers, either individually, in specific combinations, or collectively, provide a set of potential markers that can be used as a profile to identify a pregnancy with a trisomy An alternate statistical tool more often utilised in reporting clinical analytics particularly where individual tests are highly variable, is the multiple of the median (MoM). This is used to describe how an individual test deviates from the median of unaffected patients. Application of the MoM analysis to the top significant features based on p-value provides an alternative discriminatory technique to distinguish the trisomy susceptible pregnancies. FIGS. 3A and B represents the MoM box-plot for each feature showing either an upregulated or down regulated response. The calculation of MoM performed by dividing each response of the feature by the respective median response for the unaffected population. As an example, for feature index #26 the median response for the unaffected population of $4.368e^6$ was used to divide all individual case responses to give a MoM value. These MoM values for each case were used to generate a box-plot where the box identifies the inter-quartile range. Features for 3A; index #19, 367.3; index #26, 369.3; index #42, 429.4; index #43, 429.4; index #46, 445.4; index #186, 680.6; index #213, 703.6; index #222, 711.6; index #241, 727.6; & index #510, 890.8. For 3B index #44, 431.4; index #175, 670.6 & index #196, 688.6.

For identification purposes, the online database search tool provided by Lipidmaps consortium at the following link was used: http://www.lipidmaps.org/tools/ms/LMSD_search_mass_options.php to compare the MS pseudomolecular ions to assign identities to the nearest tolerance in ppm. In some cases where fragmentation patterns (data not shown) didn't match, the structure was assigned manually.

The identities of the most significant molecules as expressed in MoMs, are tentatively identified in Table 1. Each lipid metabolite was identified based on a combination of accurate mass, fragmentation mechanisms and literature references.

TABLE 1

Identification of most significant compounds relating to MOM analysis

| Row | Index | m/z | Ret. Time | Fold change | assigned structure | alternative structure |
|---|---|---|---|---|---|---|
| 1 | 213 | 703.5580 | 15.93 | 6.1 | Cholesterol ester of C22:3 | Cholesterol ester of dihydroxylated C20:5 |
| 2 | 26 | 369.3491 | 15.96 | 8.5 | Cholesterol (in-source fragmentation) | |
| 3 | 19 | 367.3312 | 15.97 | 9.6 | 7-dehydro-cholesterol (in-source fragmentation) | |

Based on the analyses undertaken, lipid markers with the following assigned m/z (+/−a mass tolerance of 20 ppm) and/or retention times represent a set of markers that could be used individually, in specific combinations, or collectively to identify an affected foetus with a trisomy, as shown in Table 2:

TABLE 2

| m/z | Ret. Time | m/z | Ret. Time |
|---|---|---|---|
| 703.5580 | 15.93 | 1202.3250 | 16.01 |
| 369.3491 | 15.96 | 431.3875 | 13.34 |
| 367.3312 | 15.97 | 429.3726 | 13.65 |
| 680.5953 | 15.93 | 844.6007 | 12.35 |
| 687.5651 | 15.98 | 688.5950 | 15.64 |
| 445.3648 | 13.46 | 890.7703 | 16.15 |
| 445.3633 | 12.55 | 1276.3440 | 16.22 |
| 727.5567 | 15.91 | 711.5619 | 16.01 |
| 429.3706 | 12.19 | 1128.3140 | 15.82 |
| 1202.325 | 16.01 | 670.6080 | 15.24 |

Example 2—Kits

Typically, a kit for use in a method as described herein will contain one or more of standards, calibrators, reagents and instructions/methodology for the extraction and/or analysis of lipids from a biological sample, such as serum.

Software may also be included containing statistical methods to predict the sample as being within unaffected ranges or likely to be affected.

Extraction of a sample is typically performed in the presence of multiple standards, such as those made up of a mixture of stable isotopes and/or nonphysiological lipids (eg deuterated (d4) lyso-phosphatidylcholine, 0.125 μg/20 uL of serum sample, Avanti Polar Lipids Inc.). The extraction may be performed using a stable isotope dilution method to determine the relative amounts of each lipid species and the method as described herein using Folch extraction (for example as outlined in Example 1).

Typically, quantitative analysis of the compounds that differentiate between unaffected and presence of a trisomy may be by using the exact masses of the parent lipids with small error tolerances of <20 ppm. Alternatively a lower resolution instrument may be used instead to monitor the parent and their fragment(s) as an MRM pair (multiple reaction mode). The determination of the relative concentration levels of each lipid species is by comparison against the assigned standard in either MS or MS/MS mode using either a single point calibrator or a standard curve if more accurate concentrations are required.

Example 3—Risk Assessment for Trisomy 21 Based on Likelihood Ratio

Determination of an increased risk pregnancy made by determining a likelihood ratio (LR) calculated from an algorithm of the form:

$$LR=i[\ln(\text{MoM lipid}i)]+j[\ln(\text{MoMlipid}j)]+k[\ln(\text{MoM-lipid}k)]+ \ldots n[\ln(\text{MoMlipid}n)]+n+1[\ln(n+1\text{MoMlipid}n+1)].$$

This LR can either be used to modify an age related risk (the prior odds typically derived from maternal age using a published age-risk formula) or as a single action point.

An example of this using Discriminant Analysis to generate standardised canonical Discriminant function coefficients $-11.6(\ln \text{MoM}_{index\ \#19}) +9.931(\ln \text{MoM}_{index\ \#26}) -0.972(\ln \text{MoM}_{index\ \#42}) -0.191(\ln \text{MoM}_{index\ \#43}) -0.176(\ln \text{MoM}_{index\ \#44}) +4.524(\ln \text{MoM}_{index\ \#45})+1.605(\ln \text{MoM}_{index\ \#46}) -1.777(\ln \text{MoM}_{index\ \#175}) +1.679(\ln \text{MoM}_{index\ \#186}) -2.12(\ln \text{MoM}_{index\ \#195}) -0.669 \ln \text{MoM}_{index\ \#196}) +5.00(\ln \text{MoM}_{index\ \#213}) -2.55(\ln \text{MoM}_{index\ \#222}) -8.137(\ln \text{MoM}_{index\ \#241}) -0.641(\ln \text{MoM}_{index\ \#510}) -0.415(\ln \text{MoM}_{index\ \#592}) +0.202(\ln \text{MoM}_{index\ \#593}) +0.428(\ln \text{MoM}_{index\ \#595}) +0.238(\ln \text{MoM}_{index\ \#596})$. Such a Discriminant analysis gives values as depicted in FIG. 3.

Alternatively the determination of an increased risk pregnancy for trisomy 21 can be made using a lipid profile where a specific pattern of lipids that are either up or down regulated compared to an unaffected pregnancy. An example of profiling is given in FIGS. 3A & 3B where the statistical conversion of the signal response (peak area or height) of each lipid species to a multiple of the median (MoM). The medium signal response of the unaffected population is used to generate a MoM given as [lipid$_{response\ area}$]/[lipid median$_{response\ area\ unaffected}$ of each lipid for the unaffected population].

Algorithms may run on a computer processing means using suitable software. For example, the software may be written in R or Java, but other software may be utilised such as JavaScript or PHP for web-based applications. The software system may include a hosted/server based component, such as SQL.

In conclusion, we have demonstrated that there exist lipid compound(s) that can be measured in maternal serum to distinguish between a pregnancy with a trisomy (21) fetus and an unaffected normal pregnancy. By use of standard statistical procedures, for example multivariate analysis, multiples of the median and/or PCA, these features can be used to discriminate between an affected and normal pregnancy, for example, lipid compound(s) identified as cholesterol and cholesterol esters and isomers thereof.

Example 4—Further Analyses Using +ve TOFMS with Results Normalised Against SM(d18:1/12:0) and PC(17:0)/14:1

Patient samples (positive for T21 or age matched controls) were extracted using Folch extraction or while MTBE extraction. MTBE refers to 9:3 MTBE:Methanol extracting solvents, the other solvent being the Folch reagent, as described herein.

The procedure utilised was as follows: 25 μl sera, 25 ul water and 25 μl of approx. 1000 ng ml standards mixture was extracted with either 1 ml of 10:3 MTBE:Methanol or 2:1 CHCl3:Methanol. Solvent was added to the spiked serum and samples were left overnight at 4° C., after a 10 minute vigorous mechanical shake. Then 200 ul of 0.1M KCl was added and samples were centrifuged at 4000 RPM for 5 minutes, layers separated and evaporated in a 5 ml glass test tube at 40° C. Reconstitution was in 100 ul of MP-B (100% IPA, 7.5 mM NH4FA) and then 200 ul of MP-A (3:1 methanol:water, 7.5 mM NH$_4$FA). 4 ul was injected, followed by HPLC essentially as described previously herein.

Figure 4:
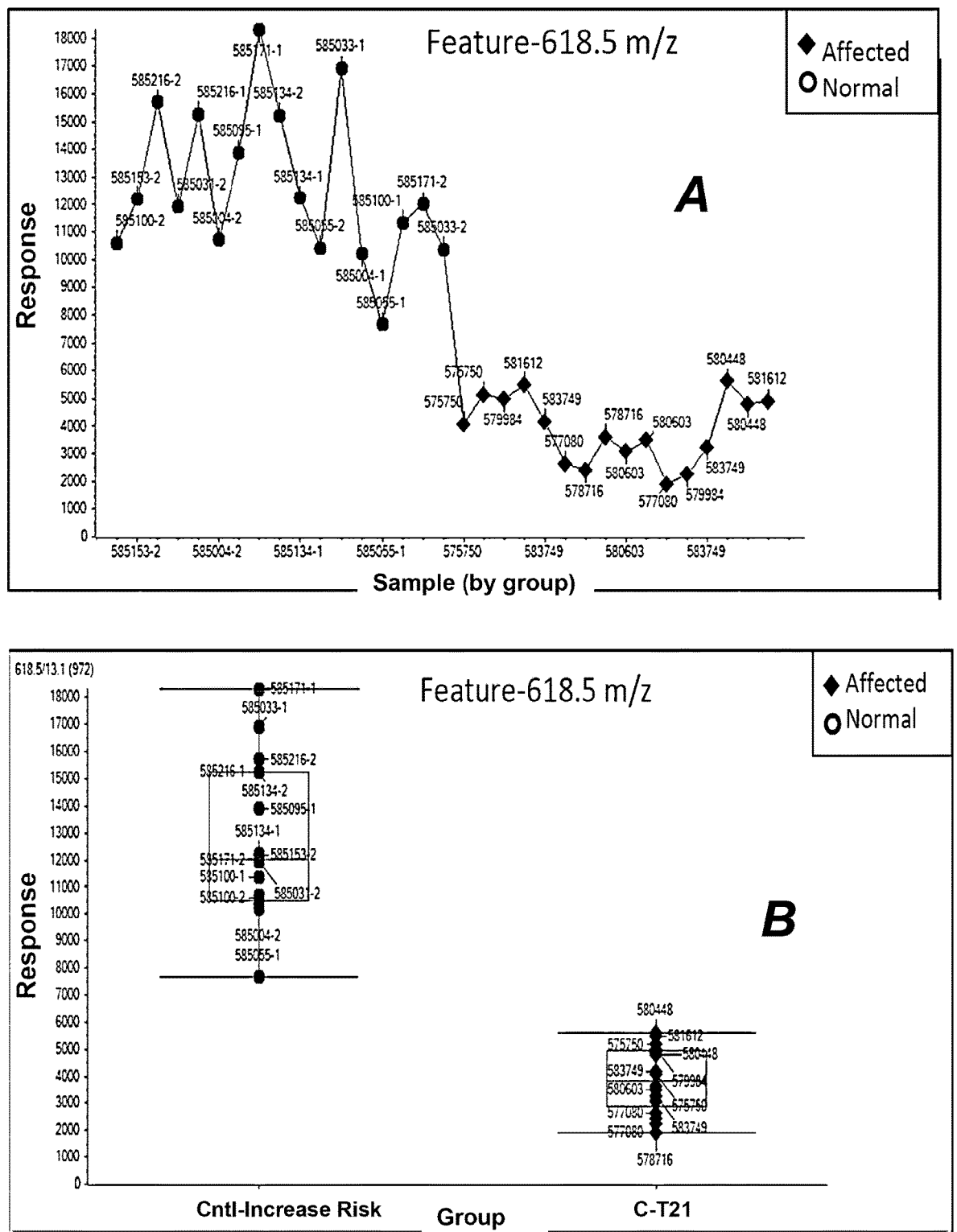
FIG. 4 shows the data for feature mass 618.5444 between T21 and controls.

FIG. 4 shows the data for feature mass 618.5444. FIG. 5 shows the data for feature mass 481.3239. FIG. 6 shows the data for feature mass 626.4947. FIG. 8 shows the data for feature mass 555.5448. The data confirms that these lipids were differentially expressed between T21 and control Example 5—Additional Lipid Markers Identified A set of additional lipid markers was identified from ten T21 patients with aged matched controls, and analysed in duplicate essentially as described in Example 4.

The data is shown in Table 3.

TABLE 3

| m/z | Regulation |
| --- | --- |
| 340.3576 | Up Regulated |
| 355.2511 | Up Regulated |
| 363.2531 | Up Regulated |
| 390.7783 | Down Regulated |
| 399.3453 | Up Regulated |
| 404.7929 | Down Regulated |
| 407.2269 | Up Regulated |
| 408.3136 | Up Regulated |
| 427.3771 | Up Regulated |
| 429.2121 | Up Regulated |
| 447.3448 | Up Regulated |
| 447.3460 | Up Regulated |
| 461.3620 | Up Regulated |
| 469.3597 | Up Regulated |
| 471.4063 | Up Regulated |
| 473.3184 | Up Regulated |
| 478.3545 | Up Regulated |
| 481.3239 | Down Regulated |
| 489.4134 | Up Regulated |
| 506.4412 | Up Regulated |
| 530.5135 | Up Regulated |
| 544.5071 | Up Regulated |
| 551.5172 | Up Regulated |
| 555.4646 | Up Regulated |
| 558.5448 | Up Regulated |
| 568.4784 | Up Regulated |
| 579.4305 | Up Regulated |
| 603.4949 | Up Regulated |
| 604.5660 | Up Regulated |
| 607.5640 | Up Regulated |
| 618.5444 | Up Regulated |
| 626.4976 | Up Regulated |
| 640.5345 | Up Regulated |
| 640.5699 | Up Regulated |
| 647.5577 | Up Regulated |
| 676.4879 | Up Regulated |
| 684.5594 | Up Regulated |
| 700.5542 | Up Regulated |
| 728.5875 | Up Regulated |
| 740.5176 | Up Regulated |
| 744.5807 | Up Regulated |
| 772.6135 | Up Regulated |
| 780.5458 | Down Regulated |

TABLE 3-continued

| m/z | Regulation |
| --- | --- |
| 788.6118 | Up Regulated |
| 798.5637 | Down Regulated |
| 817.5510 | Down Regulated |
| 816.6401 | Up Regulated |
| 820.5947 | Down Regulated |
| 826.5947 | Down Regulated |
| 832.6303 | Up Regulated |
| 834.5978 | Down Regulated |
| 850.5523 | Up Regulated |
| 860.6632 | Up Regulated |
| 864.5363 | Down Regulated |
| 876.6591 | Up Regulated |
| 902.5855 | Up Regulated |
| 904.6889 | Up Regulated |
| 904.6932 | Up Regulated |
| 920.6888 | Up Regulated |
| 928.5873 | Down Regulated |
| 948.7143 | Up Regulated |
| 964.7115 | Up Regulated |
| 992.7408 | Up Regulated |
| 1008.7339 | Up Regulated |
| 1036.7696 | Up Regulated |
| 1052.7680 | Up Regulated |
| 1078.9686 | Up Regulated |

As can be seen a variety of lipid markers (and having a mass tolerance +/−20 ppm) were either up regulated or down regulated in T21.

As used herein, the singular forms "a," "an," and "the" may refer to plural articles unless specifically stated otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

All methods described herein can be performed in any suitable order unless indicated otherwise herein or clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

The description provided herein is in relation to several embodiments which may share common characteristics and features. It is to be understood that one or more features of one embodiment may be combinable with one or more features of the other embodiments. In addition, a single feature or combination of features of the embodiments may constitute additional embodiments.

The subject headings used herein are included only for the ease of reference of the reader and should not be used to limit the subject matter found throughout the disclosure or the claims. The subject headings should not be used in construing the scope of the claims or the claim limitations.

Although the present disclosure has been described with reference to particular examples, it will be appreciated by those skilled in the art that the disclosure may be embodied in many other forms.

Future patent applications may be filed on the basis of the present application, for example by claiming priority from the present application, by claiming a divisional status and/or by claiming a continuation status. It is to be understood that the following claims are provided by way of example only, and are not intended to limit the scope of what may be claimed in any such future application. Nor should the claims be considered to limit the understanding of (or exclude other understandings of) the present disclosure. Features may be added to or omitted from the example claims at a later date.

The invention claimed is:

1. A method of screening for a fetal trisomy in a pregnant female subject, the method comprising:
exposing a serum sample obtained from the subject in the first trimester of pregnancy to one or more organic solvents and extracting lipids from the sample;
measuring the level of specific lipids in the extracted lipids by mass spectrographic analysis;
using a computer processor comprising instructions that when executed by the processor cause the processor to compare data associated with the level of the specific lipids with data associated with the level of lipids known to be indicative of the risk of a fetal trisomy, the data associated with the level of lipids known to be indicative of the risk of a fetal trisomy being held in computer readable memory; and
determining the risk of a fetal trisomy in the subject on the basis of the risk determined by the computer processor.

2. The method according to claim 1, wherein the subject is determined to have an increased risk of a fetal trisomy, a low or normal risk of a fetal trisomy, and/or the presence or absence of a fetal trisomy.

3. The method according to claim 1, wherein the fetal trisomy comprises trisomy 21.

4. The method according to claim 1, wherein the method comprises determination of the mass of the specific lipids and/or one or more fragments and/or adducts of the specific lipids.

5. The method according to claim 1, wherein the specific lipids comprise one or more of a phoshopholipid, a glycerolipid, a glycerophospholipid, a sphingolipid, a ceramide, a sterol, a glycosphingolipid, a dolicol, a lysolipid, a fatty acid, a triacylglyceride, a diacylglycerides, a monacylglycerides, an isoprenoid, a prostanoid, an eicosanoid, a sterol derivatives, a prenol lipid, a saccharolipid, a saturated fatty acid, a long chain saturated fatty acid, an unsaturated fatty acid, a polyunsaturated fatty acid, a long chain polyunsaturated fatty acid, a cholesterol and isomers thereof, a dehydrocholesterol and isomers thereof, a cholesterol esters and isomers thereof, a dehydrocholesterol esters and isomers thereof, a lyso derivative of any of the aforementioned lipid markers, and/or a fragment of any of the aforementioned lipid markers.

6. The method according to claim 1, wherein one or more of the specific lipids comprise a lipid with one or more ions with the following assigned m/z: 703.5580, 369.3491, 367.3312, 680.5953, 687.5651, 445.3648, 445.3633, 727.5567, 429.3706, 1202.3250, 431.3875, 429.3726, 844.6007, 688.5950, 890.7703, 1276.3440, 711.5619, 1128.3140, 670.6080, and/or one or more of the aforementioned lipid markers with a mass tolerance of +/−20 ppm, and/or a substantially similar m/z.

7. The method according to claim 1, wherein one or more specific lipids comprise a lipid with one or more ions with the following assigned m/z: 340.3576, 355.2511, 363.2531, 390.7783, 399.3453, 404.7929, 407.2269, 408.3136, 427.3771, 429.2121, 447.3448, 447.3460, 461.3620, 469.3597, 471.4063, 473.3184, 478.3545, 481.3239; 489.4134, 506.4412, 530.5135, 544.5071, 551.5172, 555.4646, 558.5448, 568.4784, 579.4305, 603.4949, 604.5660, 607.5640, 618.5444, 626.4976, 640.5345, 640.5699, 647.5577, 676.4879, 684.5594, 700.5542, 728.5875, 740.5176, 744.5807, 772.6135, 780.5458, 788.6118, 798.5637, 817.5510, 816.6401, 820.5947, 826.5947, 832.6303, 834.5978, 850.5523, 860.6632, 864.5363, 876.6591, 902.5855, 904.6889, 904.6932, 920.6888, 928.5873, 948.7143, 964.7115, 992.7408, 1008.7339, 1036.7696, 1052.7680, 1078.9686, 670.6080, and/or one or more of the aforementioned lipid markers with a mass tolerance of +/−20 ppm, and/or a substantially similar m/z.

8. The method according to claim 1, wherein the method comprises transferring the data associated with the levels of the specific lipids over the internet to the computer processor.

9. The method according to claim 1, wherein the method is used to identify the presence or absence of a fetal trisomy, to identify a fetal trisomy in the subject, to exclude the presence of a fetal trisomy in the subject, to identify an increased risk of a fetal trisomy, and/or to identify a low or normal risk of a fetal trisomy.

10. A method of determining the risk of a pregnant female subject carrying a fetus with a trisomy, the method comprising:
- exposing a serum sample obtained from the subject in the first trimester of pregnancy to one or more organic solvents and extracting lipids from the sample;
- measuring the level of specific lipids in the extracted lipids by mass spectrographic analysis;
- using a computer processor comprising instructions that when executed by the processor cause the processor to compare data associated with the level of the specific lipids with data associated with the level of lipids known to be indicative of the risk of a fetal trisomy, the data associated with the level of lipids known to be indicative of the risk of a fetal trisomy being held in computer readable memory;
and
- determining the risk of the subject carrying a fetus with a trisomy on the basis of the risk determined by the computer processor.

* * * * *